US007507761B2

(12) United States Patent
Sebille et al.

(10) Patent No.: US 7,507,761 B2
(45) Date of Patent: Mar. 24, 2009

(54) BENZOPYRAN DERIVATIVES, METHOD OF PRODUCTION AND USE THEREOF

(75) Inventors: Sophie Sebille, Huy (BE); Bernard Pirotte, Oupeye (BE); Stéphane Boverie, La neuville-haux-joutes (FR); Pascal De Tullio, Jupille-sue-Meuse (BE); Philippe Lebrun, Brussels (BE); Marie-Hélène Antoine, Brussels (BE)

(73) Assignees: Universite de Liege, Angleur (BE); Universite Libre de Bruxelles, Brussels (BE)

( * ) Notice: Subject to any disclaimer, the term of this patent is extended or adjusted under 35 U.S.C. 154(b) by 69 days.

(21) Appl. No.: 10/588,265

(22) PCT Filed: Jan. 21, 2005

(86) PCT No.: PCT/EP2005/050275

§ 371 (c)(1),
(2), (4) Date: Aug. 31, 2006

(87) PCT Pub. No.: WO2005/075463

PCT Pub. Date: Aug. 18, 2005

(65) Prior Publication Data

US 2007/0112063 A1   May 17, 2007

(30) Foreign Application Priority Data

Feb. 3, 2004   (EP)   ................... 04075293

(51) Int. Cl.
*A61K 31/353*   (2006.01)
*C07D 311/68*   (2006.01)
*C07D 311/70*   (2006.01)

(52) U.S. Cl. .................. 514/456; 514/337; 514/444; 546/282.7; 549/60; 549/345; 549/404

(58) Field of Classification Search ................ 549/404, 549/60, 345; 514/456, 337, 444
See application file for complete search history.

(56) References Cited

U.S. PATENT DOCUMENTS 5,276,168 A * 1/1994 Atwal ..................... 549/404

FOREIGN PATENT DOCUMENTS

EP   0480257 A2   4/1992
EP   0489404 A2   6/1992

OTHER PUBLICATIONS

Atwal et al, J. Med. Chem. 36, 1993, pp. 3971-3974, Cardio-selective Anti-Ischemic ATP-Sensitive . . . , XP-001180874.
Atwal et al, J. Med. Chem. 38, 1995, pp. 1966-1973, Cardio-selective Anti-Ischemic ATP-Sensitive . . . , XP-002278353.
Ashwood et al, J. Med. Chem. 34, 1991, pp. 3261-3267, Synthesis and Antihypertensive Activity of Pyran Oxygen . . . , XP-002034759.
Atwal et al, J. Med. Chem. 38, pp. 3236-3245, Cardioselective Anti-Ischemic ATP-Sensitive Potassium . . . , XP-009030005.
Burrell et al, Bioorganic & Med. Chem. Ltrs., vol. 3, No. 6, 1993 pp. 999-1002, Benzopryan Potassium Channel . . . , XP-001180869.

* cited by examiner

*Primary Examiner*—Bernard Dentz
(74) *Attorney, Agent, or Firm*—Jacobson Holman PLLC

(57) ABSTRACT

The invention relates to novel benzopyran derivatives of formula I, to their method of production, to composition comprising the derivatives and use thereof.

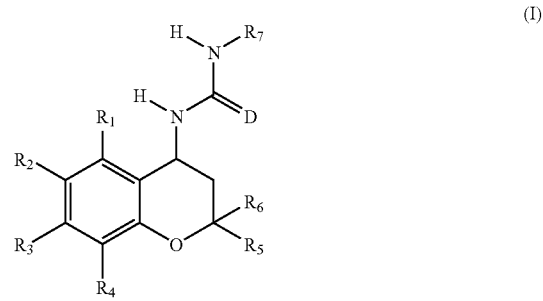

wherein:
$R_1$, $R_2$, $R_3$ and $R_4$ are independently hydrogen, halogen, $C_{1-6}$-alkyl, $C_{3-8}$-cycloalkyl, hydroxy, $C_{1-6}$-alkoxy, $C_{1-6}$-alkoxy-$C_{1-6}$-alkyl, nitro, amino, cyano, cyanomethyl, perhalomethyl, $C_{1-6}$-monoalkyl- or dialkylamino, sulfamoyl, $C_{1-6}$-alkylthio, $C_{1-6}$-alkylsulfonyl, $C_{1-6}$-alkylsulfinyl, formyl, $C_{1-6}$-alkylcarbonylamino, $R_8$arylthio, $R_8$arylsulfinyl, $R_8$arylsulfonyl, $C_{1-6}$-alkoxycarbonyl, $C_{1-6}$-alkoxycarbonyl-$C_{1-6}$-alkyl, carbamoyl, carbamoylmethyl, $C_{1-6}$-monoalkyl- or dialkylaminocarbonyl, $C_{1-6}$-monoalkyl- or dialkylaminothiocarbonyl, ureido, $C_{1-6}$-monoalkyl- or dialkylaminocarbonylamino, thioureido, $C_{1-6}$-monoalkyl- or dialkylaminothiocarbonylamino, $C_{1-6}$-monoalkyl- or dialkylaminosulfonyl, carboxy, carboxy-$C_{1-6}$-alkyl, acyl, $R_8$aryl, $R_8$aryl-$C_{1-6}$-alkyl, $R_8$aryloxy;
$R_5$ and $R_6$ are each independently hydrogen, $C_{1-6}$-alkyl or, $R_5$ and $R_6$ taken together with the carbon atom to which they are attached form a 3- to 6-membered carbocyclic ring;
$R_7$ is 2-, 3- or 4-pyridyl optionally mono- or polysubstituted by $R_1$;
$R_7$ is 2- or 3-thienyl optionally mono- or polysubstituted by $R_1$ or
$R_7$ is phenyl optionally mono- or polysubstituted by $R_1$ with the exception of or $R_7$ representing $C_6H_5$;
$R_8$ is hydrogen, halogen, $C_{1-6}$-alkyl, $C_{3-8}$-cycloalkyl, hydroxy, $C_{1-6}$-alkoxy, nitro, amino, cyano, cyanomethyl, perhalomethyl;
or a salt thereof with a pharmaceutically acceptable acid or base, or any optical isomer or mixture of optical isomers, including a racemic mixture or any polymorphic and tautomeric form.

14 Claims, No Drawings

BENZOPYRAN DERIVATIVES, METHOD OF PRODUCTION AND USE THEREOF

This is a nationalization of PCT/EP05/050275 filed Jan. 21, 2005 and published in English.

The present invention relates to novel benzopyran derivatives, to their method of production, to composition comprising the derivatives and use thereof.

ATP-sensitive potassium channels ($K_{ATP}$ channels) are of particular interest. Such channels are present in multiple cell types including endocrine cells, skeletal and smooth muscle cells, cardiac cells and central neurons. $K_{ATP}$ channels are involved in main physiological processes such as hormone secretion, smooth muscle cell contractile activity, myocardial protection and neurotransmitters release.

Several compounds are known to activate $K_{ATP}$ channels and have been named "potassium channel openers" ($PCO_s$).

Potassium channel openers are known to be able to relax vascular smooth muscles and have therefore been used for the treatment of hypertension.

It is well known that the vasorelaxant activity of benzopyran PCOs such as cromakalim (FIG. 1) is partly due to the presence of an OH group in the 3-position of the heterocycle.

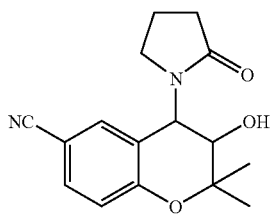

FIG. 1

Moreover, cromakalim is poorly active as an inhibitor of insulin secretion reflecting a poor activity as a PCO on the pancreatic $K_{ATP}$ channels.

We have now found novel benzopyran derivatives without an OH group in the 3-position of the benzopyran ring but bearing an arylurea or arylthiourea group in the 4-position useful as potassium channel activators which produce relaxant activity on smooth muscle cells and surprisingly are also active on the pancreatic endocrine tissue as inhibitors of insulin secretion.

In accordance with the present invention, it is provided novel benzopyran derivatives having the general formula (I)

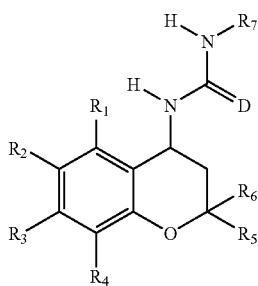

(I)

wherein:
D represents S or O;
$R_1$, $R_2$, $R_3$ and $R_4$ are independently hydrogen, halogen, $C_{1-6}$-alkyl, $C_{3-8}$-cycloalkyl hydroxy, $C_{1-6}$-alkoxy, $C_{1-6}$-alkoxy-$C_{1-6}$-alkyl, nitro, amino, cyano, cyanomethyl, perhalomethyl, $C_{1-6}$-monoalkyl- or dialkylamino, sulfamoyl, $C_{1-6}$-alkylthio, $C_{1-6}$-alkylsulfonyl, $C_{1-6}$-alkylsulfinyl, formyl, $C_{1-6}$-alkylcarbonylamino, $R_8$arylthio, $R_8$arylsulfinyl, $R_8$arylsulfonyl, $C_{1-6}$-alkoxycarbonyl, $C_{1-6}$-alkoxycarbonyl-$C_{1-6}$-alkyl, carbamoyl, carbamoylmethyl, $C_{1-6}$-monoalkyl- or dialkylaminocarbonyl, $C_{1-6}$-monoalkyl- or dialkylaminothiocarbonyl, ureido, $C_{1-6}$-monoallyl- or dialkylaminocarbonylamino, thioureido, $C_{1-6}$-monoalkyl- or dialkylaminothiocarbonylamino, $C_{1-6}$-monoalkyl- or dialkylaminosulfonyl, carboxy, carboxy-$C_{1-6}$-alkyl, acyl, $R_8$aryl, $R_8$aryl-$C_{1-6}$-alkyl, $R_8$aryloxy;

$R_5$ and $R_6$ are each independently hydrogen, $C_{1-6}$-alkyl or, $R_5$ and $R_6$ taken together with the carbon atom to which they are attached form a 3- to 6-membered carbocyclic ring;

$R_7$ is phenyl mono- or polysubstituted by $R_1$ with the exception of $R_7$ representing $C_6H_5$ or $R_7$ is 2-, 3- or 4-pyridyl optionally mono- or polysubstituted by $R_1$ or $R_7$ is 2- or 3-thienyl optionally mono- or polysubstituted by $R_1$;

$R_8$ is hydrogen, halogen, $C_{1-6}$-alkyl, $C_{3-8}$-cycloalkyl, hydroxy, $C_{1-6}$-alkoxy, nitro, amino, cyano, cyanomethyl, perhalomethyl;

Within its scope the invention includes all optical isomers of benzopyran derivatives of formula (I), some of which are optically active, and also their mixtures including racemic mixtures thereof.

The scope of the invention also includes all polymorphic forms and all tautomeric forms of the benzopyran derivatives of formula (I) such as the following tautomeric structures.

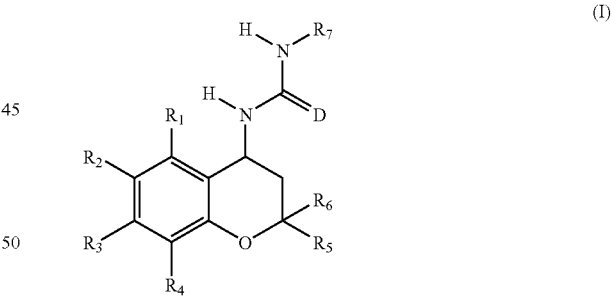

(I)

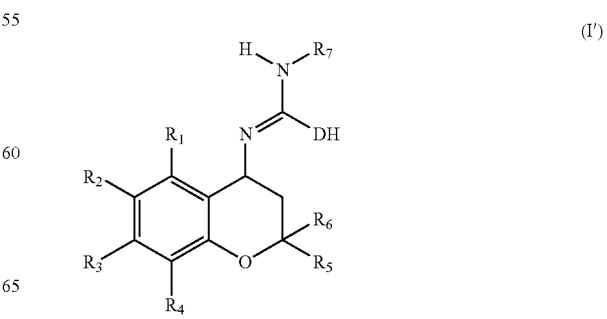

(I')

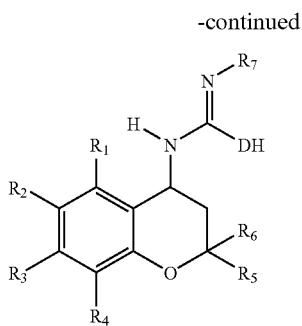

(I″)

The salts include pharmaceutically acceptable acid addition salts, pharmaceutically acceptable metal salts, or optionally alkylated ammonium salts, such as hydrochloric, hydrobromic, hydroiodic, phosphoric, sulfuric, trifluoroacetic, trichloroacetic, oxalic, maleic, pyruvic, malonic, succinic, citric, tartaric, fumaric, mandelic, benzoic, cinnamic, methanesulfonic, ethanesulfonic, picric and the like, and include acids related to the pharmaceutically acceptable salts listed in Journal of Pharmaceutical Science, 66, 2 (1977) and incorporated herein by reference, or lithium, sodium, potassium, magnesium and the like.

The term "halo" or "halogen" refers to fluorine, chlorine, bromine or iodine.

The term "$C_{1-6}$-alkyl" as used herein, alone or in combination, refers to a straight or branched, saturated hydrocarbon chain having 1 to 6 carbon atoms such as e.g. methyl, ethyl, n-propyl, isopropyl, n-butyl, sec-butyl, isobutyl, tert-butyl, n-pentyl, 2-methylbutyl, 3-methylbutyl, n-hexyl, 4-methylpentyl, neopentyl, n-hexyl, 1,2-dimethylpropyl, 2,2-dimethylpropyl, 1,2,2-trimethylpropyl, and the like.

The term "$C_{3-8}$-cycloalkyl" as used herein, alone or in combination, refers to a radical of a saturated cyclic hydrocarbon with an indicated number of carbon such as cyclopropyl, cyclobutyl, cyclopentyl or cyclohexyl.

The term "$C_{1-6}$-alkoxy" as used herein, alone or in combination, refers to a straight or branched monovalent substituent comprising a $C_{1-6}$-alkyl group linked through an ether oxygen having its free valence bond from the ether oxygen and having 1 to 6 carbon atoms e.g. methoxy, ethoxy, propoxy, isopropoxy, butoxy, pentoxy.

The term "$C_{1-6}$-alkoxy-$C_{1-6}$-alkyl" as used herein refers to a group of 2-12 carbon atoms interrupted by an O such as e.g. —$CH_2$—O—$CH_3$, —$CH_2$—O—$CH_2$—$CH_3$, —$CH_2$—O—$CH(CH_3)_2$ and the like.

The term "$C_6H_5$" as used herein refers to a phenyl unsubstituted.

The term "perhalomethyl" means trifluoromethyl, trichloromethyl, tribromomethyl or triiodomethyl.

The term "$C_{1-6}$-monoalkylamino" as used herein refers to an amino group wherein one of the hydrogen atoms is substituted with a straight or branched, saturated hydrocarbon chain having the indicated number of carbon atoms such as e.g. methylamino, ethylamino, propylamino, n-butylamino, sec-butylamino, isobutylamino, tert-butylamino, n-pentylamino, 2-methylbutylamino, n-hexylamino, 4-methylpentylamino, neopentylamino, n-hexylamino, 2,2-dimethylpropylamino and the like.

The term "$C_{1-6}$-dialkylamino" as used herein refers to an amino group wherein the two hydrogen atoms independently are substituted with a straight or branched, saturated hydrocarbon chain having the indicated number of carbon atoms such as dimethylamino, N-ethyl-N-methylamino, diethylamino, dipropylamino, N-(n-butyl)-N-methylamino, di(n-pentyl)amino, and the like.

The term "$C_{1-6}$ alkylthio" as used herein, alone or in combination, refers to a straight or branched monovalent substituent comprising a lower alkyl group linked through a divalent sulfur atom having its free valence bond from the sulfur atom and having 1 to 6 atoms e.g. methylthio, ethylthio, propylthio, butylthio, pentylthio.

The term "sulfamoyl" refers to a —$SO_2NH_2$ group.

The term "$C_{1-6}$-alkylsulfonyl" as used herein refers to a monovalent substituent comprising a $C_{1-6}$-alkyl group linked through a sulfonyl group such as e.g. methylsulfonyl, ethylsulfonyl, n-propylsulfonyl, isopropylsulfonyl, n-butylsulfonyl, sec-butylsulfonyl, isobutylsulfonyl, tert-butylsulfonyl, n-pentylsulfonyl, 2-methylbutylsulfonyl, 3-methylbutylsulfonyl, n-hexylsulfonyl, 4-methylpentylsulfonyl, neopentylsulfonyl, n-hexylsulfonyl and 2,2-dimethylpropylsulfonyl.

The term "sulfinyl" refers to a (—S(=O)—) group.

The term "$C_{1-6}$-alkylsulfinyl" as used herein refers to a monovalent substituent comprising a straight or branched $C_{1-6}$-alkyl group linked through a sulfinyl group (—S(=O)—) such as e.g. methylsulfinyl, ethylsulfinyl, isopropylsulfinyl, butylsulfinyl, pentylsulfinyl, and the like.

The term "$C_{1-6}$-alkylcarbonylamino" as used herein refers to an amino group wherein one of the hydrogen atoms is substituted with an acyl group, such as e.g. acetamido, propionamido, isopropylcarbonylamino, and the like.

The term "$R_8$aryl" as used herein refers to phenyl, 1-naphthyl, or 2-naphthyl optionally mono- or polysubstituted with $R_8$.

The term "$R_8$aryl-$C_{1-6}$-alkyl" as used herein refers to a straight or branched saturated carbon chain containing from 1 to 6 carbon atoms substituted with an aromatic carbohydride, the aryl group optionally being mono- or polysubstituted with $R_8$, such as benzyl, phenethyl, 3-phenylpropyl, 1-naphtylmethyl, 2-(1-naphtyl)ethyl and the like.

The term "$R_8$arylthio" as used herein, alone or in combination, refers to an aryl group linked through a divalent sulfur atom having its free valence bond from the sulfur atom, the aryl group optionally being mono- or polysubstituted with $R_8$, such as e.g. phenylthio, (4-methylphenyl)thio, (2-chlorophenyl)thio, and the like.

The term "$R_8$aryloxy" as used herein refers to phenoxy, 1-naphthyloxy or 2-naphthyloxy optionally mono- or polysubstituted with $R_8$.

The term "$R_8$arylsulfinyl" as used herein refers to an aryl group linked through a sulfinyl group (—S(=O)—), the aryl group optionally being mono- or polysubstituted with $R_8$, such as e.g. phenylsulfinyl, (4-chlorophenyl)sulfinyl, and the like.

The term "$R_8$arylsulfonyl" as used herein refers to an aryl group linked through a sulfonyl group, the aryl group optionally being mono- or polysubstituted with $R_8$, such as e.g. phenylsulfonyl, tosyl, and the like.

The term "$C_{1-6}$-alkoxycarbonyl" as used herein refers to a monovalent substituent comprising a $C_{1-6}$-alkoxy group linked through a carbonyl group such as e.g. methoxycarbonyl, ethoxycarbonyl, propoxycarbonyl, isopropoxycarbonyl, n-butoxycarbonyl, sec-butoxycarbonyl, tert-butoxycarbonyl, 3-methylbutoxycarbonyl, n-hexoxycarbonyl and the like.

The term "$C_{1-6}$-monoalkylaminocarbonyl" as used herein refers to a monovalent substituent comprising a $C_{1-6}$-monoalkylamino group linked through a carbonyl group such as e.g. methylaminocarbonyl, ethylaminocarbonyl, n-propylaminocarbonyl, isopropylaminocarbonyl, n-butylaminocarbonyl, sec-butylaminocarbonyl, isobutylaminocarbonyl, tert-butylaminocarbonyl, n-pentylaminocarbonyl, 2-methylbutylaminocarbonyl, 3-methylbutylaminocarbonyl, n-hexylaminocarbonyl, 4-methylpentylaminocarbonyl, neopentylaminocarbonyl, n-hexylaminocarbonyl and 2,2-dimethylpropylaminocarbonyl.

The term "$C_{1-6}$-dialkylaminocarbonyl" as used herein refers to a monovalent substituent comprising a $C_{1-6}$-dialkylamino group linked through a carbonyl group such as dimethylaminocarbonyl, N-ethyl-N-methylaminocarbonyl, diethylaminocarbonyl, dipropylaminocarbonyl, N-(n-butyl)-N-methylaminocarbonyl, di(n-pentyl)aminocarbonyl, and the like.

The term "$C_{1-6}$-monoalkylaminothiocarbonyl" as used herein refers to a monovalent substituent comprising a $C_{1-6}$-monoalkylamino group linked through a thiocarbonyl group such as e.g. methylaminothiocarbonyl, ethylaminothiocarbonyl, n-propylaminothiocarbonyl, isopropylaminothiocarbonyl, n-butylaminothiocarbonyl, sec-butylaminothiocarbonyl, isobutylaminothiocarbonyl, tert-butylaminothiocarbonyl, n-pentylaminothiocarbonyl, 2-methylbutylaminothiocarbonyl, 3-methylbutylaminothiocarbonyl, n-hexylaminothiocarbonyl, 4-methylpentylaminothiocarbonyl, neopentylaminothiocarbonyl, n-hexylaminothiocarbonyl and 2-2-dimethylpropylaminothiocarbonyl.

The term "ureido" refers to a —NHCONH$_2$ group.

The term "thioureido" refers to a —NHCSNH$_2$ group.

The term "$C_{1-6}$-monoalkylaminocarbonylamino" as used herein refers to an amino group wherein one of the hydrogen atoms is substituted with a $C_{1-6}$-monoalkylaminocarbonyl group such as e.g. methylaminocarbonylamino, ethylaminocarbonylamino, n-propylaminocarbonylamino, isopropylaminocarbonylamino, n-butylaminocarbonylamino, sec-butylaminocarbonylamino, isobutylaminocarbonylamino, tert-butylaminocarbonylamino, and 2-methylbutylaminocarbonylamino.

The term "$C_{1-6}$-dialkylaminocarbonylamino" as used herein refers to an amino group wherein one of the hydrogen atoms is substituted with a $C_{1-6}$-dialkylaminocarbonyl group such as dimethylaminocarbonylamino, N-ethyl-N-methylaminocarbonylamino, diethylaminocarbonylamino dipropylaminocarbonylamino, N-(n-butyl)-N-methylaminocarbonylamino, di(n-pentyl)aminocarbonylamino, and the like.

The term "$C_{1-6}$-monoalkylaminosulfonyl" as used herein refers to a monovalent substituent comprising a $C_{1-6}$-monoalkylamino group linked through a sulfonyl group such as e.g. methylaminosulfonyl, ethylaminosulfonyl, n-propylaminosulfonyl, isopropylaminosulfonyl, n-butylaminosulfonyl, sec-butylaminosulfonyl, isobutylaminosulfonyl, tert-butylaminosulfonyl, n-pentylaminosulfonyl, 2-methylbutylaminosulfonyl, 3-methylbutylaminosulfonyl, n-hexylaminosulfonyl, 4-methylpentylaminosulfonyl, neopentylaminosulfonyl, n-hexylaminosulfonyl and 2,2-dimethylpropylaminosulfonyl.

The term "$C_{1-6}$-dialkylaminosulfonyl" as used herein refers to a monovalent substituent comprising a $C_{1-6}$-dialkylamino group linked through a sulfonyl group such as dimethylaminosulfonyl, N-ethyl-N-methylaminosulfonyl, diethylaminosulfonyl, dipropylaminosulfonyl, N-(n-butyl)-N-methylaminosulfonyl, di(n-pentyl)aminosulfonyl, and the like.

The term "$C_{3-8}$-cycloalkyl" as used herein, alone or in combination refers to a saturated carboxylic ring of 3 to 8 carbon atoms such as cyclopropyl, cyclobutyl, cyclopentyl, cyclohexyl, cycloheptyl, cyclooctyl.

The term "isothiocyanate" as used herein refers to $R_7$—N=C=S wherein $R_7$ is as described above.

Preferred benzopyran derivatives of the invention are those wherein $R_7$ is an element selected from the group consisting of (pyridyl and phenyl) and $R_1$ on $R_7$ is an element selected from the group consisting of (hydrogen, halogen, cyano and nitro).

The most preferred benzopyran derivatives are

R/S-4-(3-Chlorophenylaminothiocarbonylamino)-3,4-dihydro-2,2-dimethyl-6-fluoro-2H-1-benzopyran.

R/S-6-Chloro-4-(3-chlorophenylaminothiocarbonylamino)-3,4-dihydro-2,2-dimethyl-2H-1-benzopyran.

R/S-4-(4-Chlorophenylaminothiocarbonylamino)-3,4-dihydro-2,2-dimethyl-6-fluoro-2H-1-benzopyran.

R/S-6-Chloro-4-(4-chlorophenylaminothiocarbonylamino)-3,4-dihydro-2,2-dimethyl-2H-1-benzopyran.

R/S-6-Bromo-4-(4-chlorophenylaminothiocarbonylamino)-3,4-dihydro-2,2-dimethyl-2H-1-benzopyran.

R/S-4-(3-Cyanophenylaminothiocarbonylamino)-3,4-dihydro-2,2-dimethyl-6-fluoro-2H-1-benzopyran.

R/S-6-Chloro-4-(3-cyanophenylaminothiocarbonylamino)-3,4-dihydro-2,2-dimethyl-2H-1-benzopyran.

R/S-6-Bromo-4-(3-cyanophenylaminothiocarbonylamino)-3,4-dihydro-2,2-dimethyl-2H-1-benzopyran.

R/S-4-(4-Cyanophenylaminothiocarbonylamino)-3,4-dihydro-2,2-dimethyl-6-fluoro-2H-1-benzopyran.

R/S-6-Chloro-4-(4-cyanophenylaminothiocarbonylamino)-3,4-dihydro-2,2-dimethyl-2H-1-benzopyran.

R/S-6-Bromo-4-(4-cyanophenylaminothiocarbonylamino)-3,4-dihydro-2,2-dimethyl-2H-1-benzopyran.

R/S-6-Chloro-3,4-dihydro-2,2-dimethyl-4-(3-nitrophenylaminothiocarbonylamino)-2H-1-benzopyran.

R/S-6-Bromo-3,4-dihydro-2,2-dimethyl-4-(3-nitrophenylaminothiocarbonylamino)-2H-1-benzopyran.

R/S-3,4-Dihydro-2,2-dimethyl-6-fluoro-4-(4-nitrophenylaminothiocarbonylamino)-2H-1-benzopyran.

R/S-6-Chloro-3,4-dihydro-2,2-dimethyl-4-(4-nitrophenylaminothiocarbonylamino)-2H-1-benzopyran.

R/S-6-Bromo-3,4-dihydro-2,2-dimethyl-4-(4-nitrophenylaminothiocarbonylamino)-2H-1-benzopyran.

R/S-6-Bromo-3,4-dihydro-2,2-dimethyl-4-(3-trifluoromethylphenylaminothiocarbonylamino)-2H-1-benzopyran.

R/S-6-Chloro-3,4-dihydro-2,2-dimethyl-4-(2-methoxyphenylaminocarbonylamino)-2H-1-benzopyran.

R/S-6-Bromo-3,4-dihydro-2,2-dimethyl-4-(2-methoxyphenylaminocarbonylamino)-2H-1-benzopyran.

R/S-3,4-Dihydro-2,2-dimethyl-6-fluoro-4-(3-methoxyphenylaminocarbonylamino)-2H-1-benzopyran.

R/S-6-Chloro-3,4-dihydro-2,2-dimethyl-4-(3-methoxyphenylaminocarbonylamino)-2H-1-benzopyran.

R/S-6-Bromo-3,4-dihydro-2,2-dimethyl-4-(3-methoxyphenylaminocarbonylamino)-2H-1-benzopyran.

R/S-3,4-Dihydro-2,2-dimethyl-6-fluoro-4-(4-methoxyphenylaminocarbonylamino)-2H-1-benzopyran.

R/S-6-Chloro-3,4-dihydro-2,2-dimethyl-4-(4-methoxyphenylaminocarbonylamino)-2H-1-benzopyran.

R/S-6-Bromo-3,4-dihydro-2,2-dimethyl-4-(4-methoxyphenylaminocarbonylamino)-2H-1-benzopyran.

R/S-3,4-Dihydro-2,2-dimethyl-6-fluoro-4-(2-methylphenylaminocarbonylamino)-2H-1-benzopyran.

R/S-6-Chloro-3,4-dihydro-2,2-dimethyl-4-(2-methylphenylaminocarbonylamino)-2H-1-benzopyran.

R/S-6-Bromo-3,4-dihydro-2,2-dimethyl-4-(2-methylphenylaminocarbonylamino)-2H-1-benzopyran.

R/S-3,4-Dihydro-2,2-dimethyl-6-fluoro-4-(3-methylphenylaminocarbonylamino)-2H-1-benzopyran.

R/S-6-Chloro-3,4-dihydro-2,2-dimethyl-4-(3-methylphenylaminocarbonylamino)-2H-1-benzopyran.

R/S-6-Bromo-3,4-dihydro-2,2-dimethyl-4-(3-methylphenylaminocarbonylamino)-2H-1-benzopyran.
R/S-3,4-Dihydro-2,2-dimethyl-6-fluoro-4-(4-methylphenylaminocarbonylamino)-2H-1-benzopyran.
R/S-6-Chloro-3,4-dihydro-2,2-dimethyl-4-(4-methylphenylaminocarbonylamino)-2H-1-benzopyran.
R/S-6-Bromo-3,4-dihydro-2,2-dimethyl-4-(4-methylphenylaminocarbonylamino)-2H-1-benzopyran.
R/S-4-(2-Chlorophenylaminocarbonylamino)-3,4-dihydro-2,2-dimethyl-6-fluoro-2H-1-benzopyran.
R/S-6-Chloro-4-(2-chlorophenylaminocarbonylamino)-3,4-dihydro-2,2-dimethyl-2H-1-benzopyran.
R/S-6-Bromo-4-(2-chlorophenylaminocarbonylamino)-3,4-dihydro-2,2-dimethyl-2H-1-benzopyran.
R/S-4-(3-Chlorophenylaminocarbonylamino)-3,4-dihydro-2,2-dimethyl-6-fluoro-2H-1-benzopyran.
R/S-6-Chloro-4-(3-chlorophenylaminocarbonylamino)-3,4-dihydro-2,2-dimethyl-2H-1-benzopyran.
R/S-6-Bromo-4-(3-chlorophenylaminocarbonylamino)-3,4-dihydro-2,2-dimethyl-2H-1-benzopyran.
R/S-4-(4-Chlorophenylaminocarbonylamino)-3,4-dihydro-2,2-dimethyl-6-fluoro-2H-1-benzopyran.
R/S-6-Chloro-4-(4-chlorophenylaminocarbonylamino)-3,4-dihydro-2,2-dimethyl-2H-1-benzopyran.
R/S-6-Bromo-4-(4-chlorophenylaminocarbonylamino)-3,4-dihydro-2,2-dimethyl-2H-1-benzopyran.

The benzopyran derivatives of formula (I) and combinations thereof, can be formulated in compositions such as tablets, capsules or elixirs for oral administration, in sterile solutions or suspensions.

The benzopyran derivatives of the present invention interact with the potassium channels and hence act as openers or blockers of the ATP-regulated potassium channels, which make them useful in the treatment of various diseases of the cardiovascular system, e.g. cerebral ischemia, hypertension, ischemic heart diseases, angina pectoris and coronary heart diseases, the pulmonary system, the gastrointestinal system, the central nervous system and the endocrinological system.

Since some $K_{ATP}$ channel openers are able to antagonize vasospasms in basilar or cerebral arteries, the benzopyran derivatives of the present invention can be used for the treatment of vasospastic disorders, subarachnoid haemorrhage and migraine.

The benzopyran derivatives of the present invention may also be used for the treatment of diseases associated with decreased skeletal muscle blood flow such as Raynaud's disease and intermittent claudication.

Further, the benzopyran derivatives of the invention may be used for the treatment of chronic airway diseases, including asthma, and for treatment of detrusor muscle instability secondary to bladder outflow obstruction and therefore for kidney stones by aiding their passage along the urethra.

The present benzopyran derivatives could also be used for treatment of conditions associated with disturbances in gastrointestinal motility such as irritable bowel syndrome. Additionally, these benzopyran derivatives can be used for the treatment of premature labour and dysmenorrhea.

Potassium channel openers hyperpolarizes neurons and inhibit neurotransmitter release and it is expected that such benzopyran derivatives can be used for the treatment of various diseases of the central nervous system, e.g. epilepsia, ischemia and neurodegenerative diseases, and for the management of pain.

Further, potassium channel openers promote hair growth, therefore, the benzopyran derivatives of the present invention can be used for the treatment of baldness.

Potassium channel openers also relax urinary bladder smooth muscle, thus, the benzopyran derivatives of the present invention can be used for the treatment of urinary incontinence.

In diseases such as nesidioblastosis and insulinoma in which a hypersecretion of insulin causes severe hypoglycemia, the benzopyran derivatives of the present invention can be used to reduce insulin secretion. In obesity, hyperinsulinemia and insulin resistance is very frequently encountered. This condition could lead to the development of noninsulin dependent diabetes (NIDDM). It is expected that potassium channel openers and hence the benzopyran derivatives of the present invention can be used for reducing the hyperinsulinemia and thereby prevent diabetes and reduce obesity. In overt NIDDM, treatment of hyperinsulinemia with potassium channel openers, and hence the present benzopyran derivatives, can be of benefit in restoring glucose sensitivity and normal insulin secretion.

In early cases of insulin dependent diabetes (IDDM) or in prediabetic cases, potassium channel openers and hence the present benzopyran derivatives can be used to induce beta cell rest which may prevent the progression of the autoimmune disease.

The potassium channel openers of the present invention can be administered in combination with an immunosuppressant or with an agent like nicotinamide, which will reduce autoimmune degeneration of beta-cells.

Combining beta-cell rest with a treatment protecting the beta-cells against cytokine mediated beta-cell impairment/cytotoxicity is another aspect of this invention.

Insulin requiring or Type 1 diabetes (IDDM) as well as late onset IDDM (also known as type 1.5. e.g. non-insulin-requiring Type 2 (NIIDM) patients with autoreactivity against beta-cell epitopes that later turns insulin requiring) have circulating autoreactive monocytes/lymphocytes that homes to the islets/beta-cells and releases their cytokines. Some of these cytokines (e.g. interleukin-1β (IL-1β), tumour necrosis factor α (TNFα) and interferon γ (IFNγ)) are specifically toxic to the beta-cells, e.g. through the induction of nitric oxide (NO) and other free radicals. Inhibition of this cytotoxicity, e.g. by co-administering nicotinamide (NA), a derivative hereof or other cytokine protective compounds to the prediabetic/diabetic patients treated with the PCO compound, is an example of this aspect. Nicotinamide belongs to the B-vitamin family and is derived from nicotinic acid by amidation of the carboxyl group. It processes none of nicotine's pharmacological properties. NA is converted into NAD+, which acts as a coenzyme for proteins involved in tissue respiration. NA has been proposed to influence several of the putative intracellular molecular events following immune attack on the beta-cells. Animal experiments and early non-blinded experiments in humans have indicated a protective role of this compound against IDDM as well as in cytokine/immune mediated beta-cell destruction.

Yet another aspect of this application concerns the use of a PCO compound alone or in combination with the inhibitor of cytokine/immune mediated beta-cell impairment, in transplantation, e.g. islet transplantation into diabetes patients.

Benzopyran derivatives of the present invention which act as blockers of $K_{ATP}$-channels can be used for the treatment of NIDDM.

Preferably, the benzopyran derivatives of the present invention may be used for treatment or prevention of diseases of the endocrinological system such as hyperinsulinaemia and diabetes.

Accordingly, in another aspect the invention relates to a benzopyran derivative of the general formula I or a pharmaceutically acceptable acid addition salt thereof for use as a therapeutically acceptable substance, preferably for use as a therapeutically acceptable substance in the treatment of hyperinsulinaemia and treatment or prevention of diabetes.

Furthermore, the invention also relates to the use of benzopyran derivatives of formula I as medicaments useful for treating hyperinsulinaemia and treating or preventing diabetes.

In still another aspect, the present invention relates to methods of preparing the above mentioned compounds.

The methods comprises:
reacting a compound of formula (II)

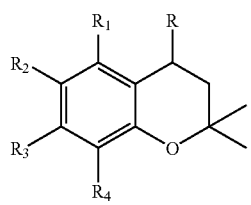
(II)

wherein R represents $NH_2$ and $R_1$, $R_2$, $R_3$ and $R_4$ are defined as for formula (I) with an isothiocyanante or an isocyanate of formula (III)

$$R_7-N=C=D \quad (III)$$

wherein D represents S or O and $R_7$ is defined as for formula (I);

reacting a compound of formula (II) wherein R represents $-N=C=S$ and $R_1$, $R_2$, $R_3$ and $R_4$ are defined as for formula (I) with an amine of formula (IV).

$$R_7-NH_2 \quad (IV)$$

Compounds of formula (II) wherein R represents $NH_2$ are prepared according to literature starting from the appropriate phenol. The method of preparation is described by Khelili, S.; Nguyen, Q.-A.; Lebrun, P.; Delarge, J. and Pirotte, B. in *Pharm. Pharmacol. Commun.* 1999, 5, 189-193, incorporated by reference and illustrated in steps i to vi of scheme 1.

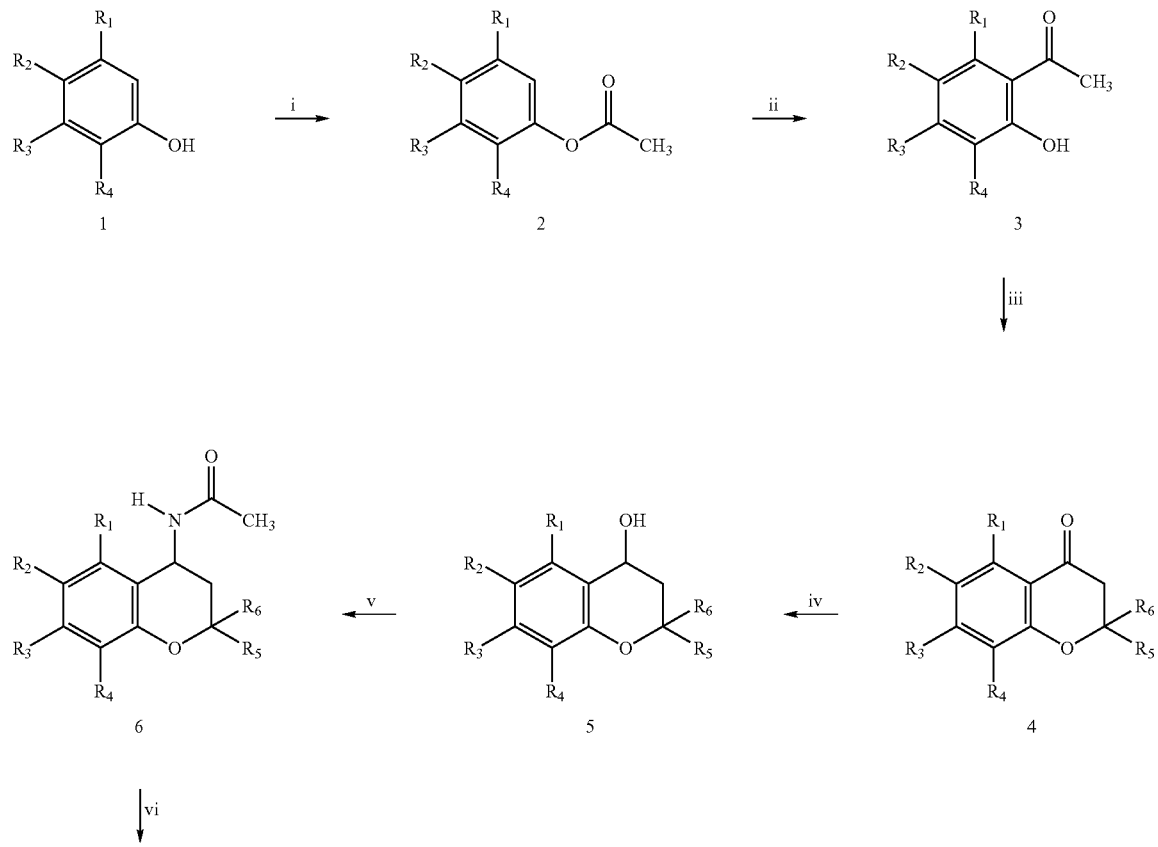

Scheme 1.

-continued

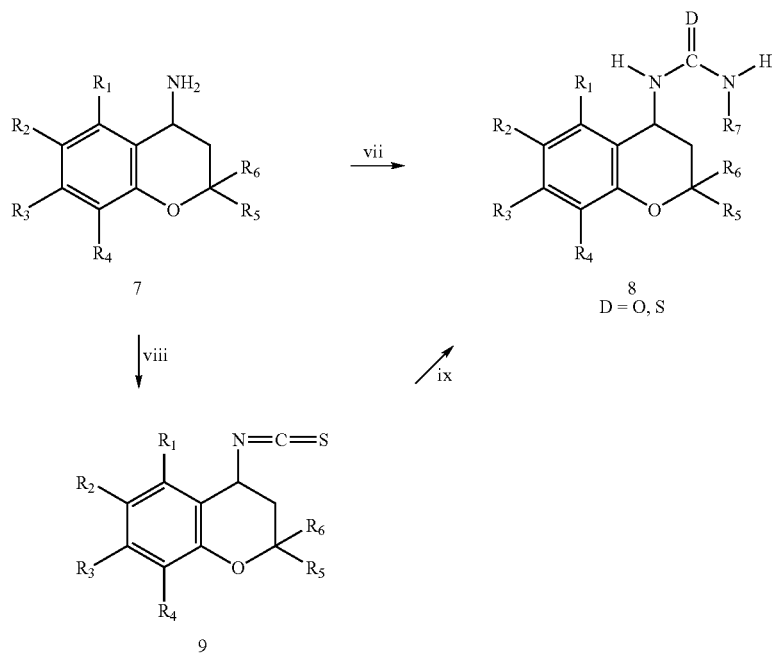

Reagents:
(i) (CH₃CO)₂O, H₂SO₄;
(ii) AlCl₃;
(iii) R₅R₆C=O, pyrrolidine;
(iv) NaBH₄, CH₃OH;
(v) CH₃CN, H₂SO₄;
(vi) HCl 37%;
(vii) R₇NCD (D = O, S), CH₂Cl₂;
(viii) 1,1′-thiocarbonyldiimidazole, 1,4-dioxane; (ix) R₇NH₂, CH₂Cl₂.

Compounds of formula (I) wherein $R_7$ represents

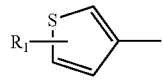

are prepared according to literature. The method of preparation is described by Barker, J.-M.; Huddleston, P.-R. and Wood, M.-L. in *Synthesis* 1977, 255, incorporated by reference and illustrated in scheme 2.

Scheme 2.

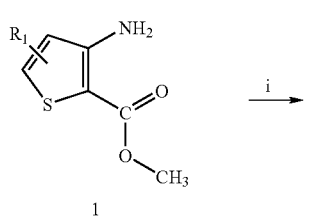

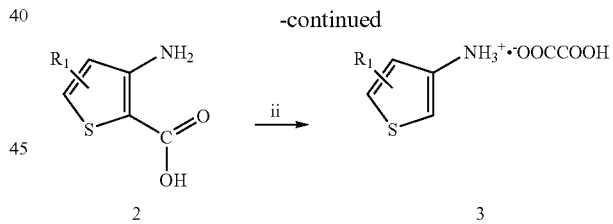

Reagents:
(i) NaOH;
(ii) oxalic acid dihydrate, 2-propanol;
(iii) NH₃;
(iv) 1,1′-thiocarbonyldiimidazole, 1,4-dioxane.

3-Thienyl isothiocyanates (5—scheme 2) are prepared by treatment of 3-aminothiophenes (4—scheme 2) with 1,1′-thiocarbonyldiimidazole in 1,4-dioxane according to the following procedure:

1,1'-Thiocarbonyldiimidazole (1.01 g, 0.00567 mol) was added to a stirred solution of 3-aminothiophene (0.55 g, 0.0056 mol) dissolved in dry 1,4-dioxane (15 mL). The mixture was refluxed under nitrogen for 20 minutes.

The solution was concentrated under reduced pressure and diethylether was added to the residue. The organic layer was washed with a 0.1 M hydrochloric acid solution. Diethylether was removed under reduced pressure. The resulting oil was used without further purification.

Compounds of formula (IV) wherein $R_7$ represents

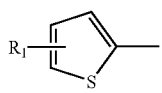

are prepared according to literature. The method of preparation is described by Binder, D.; Habison, G. and Noe, C. in *Communications* 1977, 255, incorporated by reference and illustrated in scheme 3.

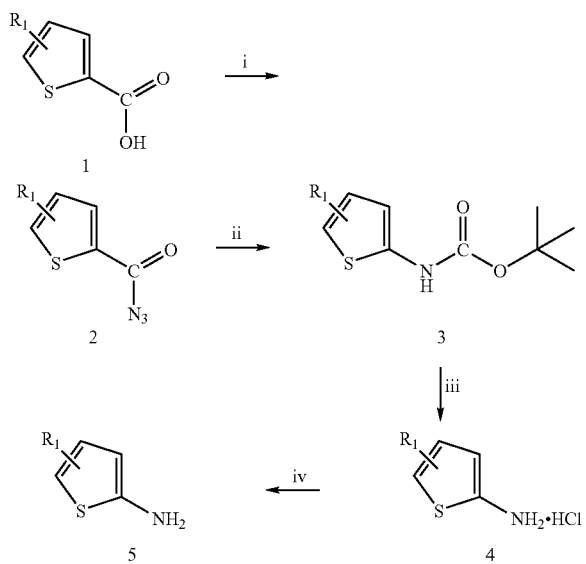

Reagents:
(i) Ethyl chloroformate, TEA, $NaN_3$;
(ii) tert-butanol, 1,4-dioxane,
(iii) HCl 37%;
(iv) NaOH 20%.

The method of preparing the compounds of formula (I) is further illustrated in scheme 1 and in the following examples which, however, are not to be construed as limiting.

Melting points were determined on a Büchi 530 capillary apparatus and are uncorrected. IR spectra were recorded as KBr pellets on a Perkin-Elmer 1000 FTIR spectrophotometer. The $^1$H NMR spectra were recorded on a Bruker AW-80 (80 MHz) instrument using $d_6$-DMSO as solvent with hexamethyldisiloxane (HMDS) as an internal standard; chemical shifts are reported in δ values (ppm) relative to internal HMDS. The abbreviation s=singulet, d=doublet, t=triplet, q=quadruplet, m=multiplet and b=broad are used throughout. Elemental analyses (C, H, N, S) were realized on a Carlo-Erba EA 1108-elemental analyzer and were within ±0.4% of the theoretical values. All reactions were routinely checked by TLC on silica gel Merck 60 $F_{524}$.

EXAMPLE 1

R/S-3,4-Dihydro-2,2-dimethyl-6-fluoro-4-(2-methylphenylaminothiocarbonylamino)-2H-1-benzopyran 2-Methylphenyl isothiocyanate (0.32 mL, 2.4 mmol) was added to a solution of R/S-4-amino-3,4-dihydro-2,2-dimethyl-6-fluoro-2H-1-benzopyran (0.4 g, 2 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried (57%). mp: 163.5-165° C., IR (KBr): υ: 3340, 3130 (N—H), 2972 (C—H aliphatic), 1191 (C═S) cm$^{-1}$, Anal. ($C_{19}H_{21}N_2OSF$) C, H, N, S.

EXAMPLE 2

R/S-6-Chloro-3,4-dihydro-2,2-dimethyl-4-(2-methylphenylaminothiocarbonylamino)-2H-1-benzopyran 2-Methylphenyl isothiocyanate (0.31 mL, 2.3 mmol) was added to a solution of R/S-4-amino-6-chloro-3,4-dihydro-2,2-dimethyl-2H-1-benzopyran (0.4 g, 1.9 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried (51%). mp: 156.5-157.5° C., IR (KBr): υ: 3345, 3130 (N—H), 2974 (C—H aliphatic), 1199 (C═S) cm$^{-1}$, Anal. ($C_{19}H_{21}N_2OSCl$) C, H, N, S.

EXAMPLE 3

R/S-6-Bromo-3,4-dihydro-2,2-dimethyl-4-(2-methylphenylaminothiocarbonylamino)-2H-1-benzopyran 2-Methylphenyl isothiocyanate (0.26 mL, 1.9 mmol) was added to a solution of R/S-4-amino-6-bromo-3,4-dihydro-2,2-dimethyl-2H-1-benzopyran (0.4 g, 1.6 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried (55%). mp: 162.5-163° C., IR (KBr): υ: 3347, 3168 (N—H), 2972 (C—H aliphatic), 1199 (C═S) cm$^{-1}$, Anal. ($C_{19}H_{21}N_2OSBr$) C, H, N, S.

EXAMPLE 4

R/S-3,4-Dihydro-2,2-dimethyl-6-fluoro-4-(3-methylphenylaminothiocarbonylamino)-2H-1-benzopyran 3-Methylphenyl isothiocyanate (0.32 mL, 2.4 mmol) was added to a solution of R/S-4-amino-3,4-dihydro-2,2-dimethyl-6-fluoro-2H-1-benzopyran (0.4 g, 2 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried (64%). mp: 137-139° C., IR (KBr): υ: 3376, 3171 (N—H), 3010 (C—H aromatic), 2977, 2922 (C—H aliphatic), 1197 (C═S) cm$^{-1}$, Anal. ($C_{19}H_{21}N_2OSF$) C, H, N, S.

EXAMPLE 5

R/S-6-Chloro-3,4-dihydro-2,2-dimethyl-4-(3-methylphenylaminothiocarbonylamino)-2H-1-benzopyran 3-Methylphenyl isothiocyanate (0.31 mL, 2.3 mmol) was added to a solution of R/S-4-amino-6-chloro-3,4-dihydro-2,2-dimethyl-2H-1-benzopyran (0.4 g, 1.9 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried (60%). mp: 151-152° C., IR (KBr): υ: 3367, 3164 (N—H), 2976 (C—H aliphatic), 1199 (C=S) cm$^{-1}$, Anal. ($C_{19}H_{21}N_2OSCl$) C, H, N, S.

EXAMPLE 6

R/S-6-Bromo-3,4-dihydro-2,2-dimethyl-4-(3-methylphenylaminothiocarbonylamino)-2H-1-benzopyran 3-Methylphenyl isothiocyanate (0.26 mL, 1.9 mmol) was added to a solution of R/S-4-amino-6-bromo-3,4-dihydro-2,2-dimethyl-2H-1-benzopyran (0.4 g, 1.6 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried (46%). mp: 160-161° C., IR (KBr): υ: 3363, 3163 (N—H), 2976 (C—H aliphatic), 1199 (C=S) cm$^{-1}$, Anal. ($C_{19}H_{21}N_2OSBr$) C, H, N, S.

EXAMPLE 7

R/S-3,4-Dihydro-2,2-dimethyl-6-fluoro-4-(4-methylphenylaminothiocarbonylamino)-2H-1-benzopyran 4-Methylphenyl isothiocyanate (0.35 g, 2.4 mmol) was added to a solution of R/S-4-amino-3,4-dihydro-2,2-dimethyl-6-fluoro-2H-1-benzopyran (0.4 g, 2 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried. The product was recrystallised in ethyl acetate:petroleum ether 40/60 (1:3) (57%). mp: 170-170.5° C., IR (KBr): υ: 3181 (N—H), 3031 (C—H aromatic), 2977, 2926 (C—H aliphatic), 1195 (C=S) cm$^{-1}$, Anal. ($C_{19}H_{21}N_2OSF$) C, H, N, S.

EXAMPLE 8

R/S-6-Chloro-3,4-dihydro-2,2-dimethyl-4-(4-methylphenylaminothiocarbonylamino)-2H-1-benzopyran 4-Methylphenyl isothiocyanate (0.34 g, 2.3 mmol) was added to a solution of R/S-4-amino-6-chloro-3,4-dihydro-2,2-dimethyl-2H-1-benzopyran (0.4 g, 1.9 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried (60%), mp: 172-173.5° C., IR (KBr): υ: 3376, 3191 (N—H), 3035 (C—H aromatic), 2975, 2924 (C—H aliphatic), 1199 (C=S) cm$^{-1}$, Anal. ($C_{19}H_{21}N_2OSCl$) C, H, N, S.

EXAMPLE 9

R/S-6-Bromo-3,4-dihydro-2,2-dimethyl-4-(4-methylphenylaminothiocarbonylamino)-2H-1-benzopyran 4-Methylphenyl isothiocyanate (0.28 g, 1.9 mmol) was added to a solution of R/S-4-amino-6-bromo-3,4-dihydro-2,2-dimethyl-2H-1-benzopyran (0.4 g, 1.6 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried (46%). mp: 176-176.5° C., IR (KBr): υ: 3373, 3189 (N—H), 3033 (C—H aromatic), 2975, 2923 (C—H aliphatic), 1198 (C=S) cm$^{-1}$, Anal. ($C_{19}H_{21}N_2OSBr$) C, H, N, S.

EXAMPLE 10

R/S-4-(2-Chlorophenylaminothiocarbonylamino)-3,4-dihydro-2,2-dimethyl-6-fluoro-2H-1-benzopyran 2-Chlorophenyl isothiocyanate (0.31 mL, 2.4 mmol) was added to a solution of R/S-4-amino-3,4-dihydro-2,2-dimethyl-6-fluoro-2H-1-benzopyran (0.4 g, 2 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried (57%). mp: 160-162° C., IR (KBr): υ: 3379, 3219 (N—H), 3025 (C—H aromatic), 2978, 2928 (C—H aliphatic), 1196 (C=S) cm$^{-1}$, Anal. ($C_{18}H_{18}N_2OSFCl$) C, H, N, S.

EXAMPLE 11

R/S-6-Chloro-4-(2-chlorophenylaminothiocarbonylamino)-3,4-dihydro-2,2-dimethyl-2H-1-benzopyran 2-Chlorophenyl isothiocyanate (0.30 mL, 2.3 mmol) was added to a solution of R/S-4-amino-6-chloro-3,4-dihydro-2,2-dimethyl-2H-1-benzopyran (0.4 g, 1.9 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried. The product was recrystallised in ethyl acetate:petroleum ether 40/60 (1:3) (42%). mp: 158-159.5° C., IR (KBr): υ: 3360, 3164 (N—H), 2975 (C—H aliphatic), 1195 (C=S) cm$^{-1}$, Anal. ($C_{18}H_{18}N_2OSCl_2$) C, H, N, S.

EXAMPLE 12

R/S-6-Bromo-4-(2-chlorophenylaminothiocarbonylamino)-3,4-dihydro-2,2-dimethyl-2H-1-benzopyran 2-Chlorophenyl isothiocyanate (0.24 mL, 1.9 mmol) was added to a solution of R/S-4-amino-6-bromo-3,4-dihydro-2, 2-dimethyl-2H-1-benzopyran (0.4 g, 1.6 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried (54%). mp: 162-163° C., IR (KBr): υ: 3368, 3164 (N—H), 2977, 2949, 2926 (C—H aliphatic), 1196 (C=S) cm$^{-1}$, Anal. ($C_{18}H_{18}N_2OSClBr$) C, H, N, S.

EXAMPLE 13

R/S-4-(3-Chlorophenylaminothiocarbonylamino)-3, 4-dihydro-2,2-dimethyl-6-fluoro-2H-1-benzopyran 3-Chlorophenyl isothiocyanate (0.31 mL, 2.4 mmol) was added to a solution of R/S-4-amino-3,4-dihydro-2,2-dimethyl-6-fluoro-2H-1-benzopyran (0.4 g, 2 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried. The product was recrystallised in ethyl acetate:petroleum ether 40/60 (1:3) (48%). mp: 171-172° C., IR (KBr): υ: 3380, 3221 (N—H), 3043 (C—H aromatic), 2977, 2931 (C—H aliphatic), 1196 (C=S) cm$^{-1}$, Anal. ($C_{18}H_{18}N_2OSFCl$) C, H, N, S.

EXAMPLE 14

R/S-6-Chloro-4-(3-chlorophenylaminothiocarbonylamino)-3,4-dihydro-2,2-dimethyl-2H-1-benzopyran 3-Chlorophenyl isothiocyanate (0.30 mL, 2.3 mmol) was added to a solution of R/S-4-amino-6-chloro-3,4-dihydro-2,2-dimethyl-2H-1-benzopyran (0.4 g, 1.9 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried (57%). mp: 161.5-163° C., IR (KBr): υ: 3339, 3159 (N—H), 3006 (C—H aromatic), 2976, 2925 (C—H aliphatic), 1199 (C=S) cm$^{-1}$, Anal. ($C_{18}H_{18}N_2OSCl_2$) C, H, N, S.

EXAMPLE 15

R/S-6-Bromo-4-(3-chlorophenylaminothiocarbonylamino)-3,4-dihydro-2,2-dimethyl-2H-1-benzopyran 3-Chlorophenyl isothiocyanate (0.24 mL, 1.9 mmol) was added to a solution of R/S-4-amino-6-bromo-3,4-dihydro-2,2-dimethyl-2H-1-benzopyran (0.4 g, 1.6 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried (68%). mp: 162-163° C., IR (KBr): υ: 3337, 3155 (N—H), 3001 (C—H aromatic), 2975, 2924 (C—H aliphatic), 1199 (C=S) cm$^{-1}$, Anal. ($C_{18}H_{18}N_2OSClBr$) C, H, N, S.

EXAMPLE 16

R/S-4-(4-Chlorophenylaminothiocarbonylamino)-3, 4-dihydro-2,2-dimethyl-6-fluoro-2H-1-benzopyran 4-Chlorophenyl isothiocyanate (0.40 g, 2.4 mmol) was added to a solution of R/S-4-amino-3,4-dihydro-2,2-dimethyl-6-fluoro-2H-1-benzopyran (0.4 g, 2 mmol) in methylene chloride (5 mL). After 30 minutes, the resulting precipitate was collected by filtration, washed with petroleum ether and dried. The crude product was triturated with ethyl acetate. The insoluble was collected by filtration and petroleum ether was added to the filtrate. The resulting precipitate was collected by filtration, washed with petroleum ether and dried. The product was recrystallised in ethyl acetate:petroleum ether 40/60 (1:3) (46%). mp: 193-194° C., IR (KBr): υ: 3237 (N—H), 3041 (C—H aromatic), 2978, 2929 (C—H aliphatic), 1197 (C=S) cm$^{-1}$, Anal. ($C_{18}H_{18}N_2OSFCl$) C, H, N, S.

EXAMPLE 17

R/S-6-Chloro-4-(4-chlorophenylaminothiocarbonylamino)-3,4-dihydro-2,2-dimethyl-2H-1-benzopyran 4-Chlorophenyl isothiocyanate (0.39 g, 2.3 mmol) was added to a solution of R/S-4-amino-6-chloro-3,4-dihydro-2,2-dimethyl-2H-1-benzopyran (0.4 g, 1.9 mmol) in methylene chloride (5 mL). After 30 minutes, the resulting precipitate was collected by filtration, washed with petroleum ether and dried. The crude product was triturated with ethyl acetate. The insoluble was collected by filtration and petroleum ether was added to the filtrate. The resulting precipitate was collected by filtration, washed with petroleum ether and dried (46%). mp: 186-187.5° C., IR (KBr): υ: 3240 (N—H), 3042 (C—H aromatic), 2983, 2933 (C—H aliphatic), 1198 (C=S) cm$^{-1}$, Anal. ($C_{18}H_{18}N_2OSCl_2$) C, H, N, S.

EXAMPLE 18

R/S-6-Bromo-4-(4-chlorophenylaminothiocarbonylamino)-3,4-dihydro-2,2-dimethyl-2H-1-benzopyran 4-Chlorophenyl isothiocyanate (0.32 g, 1.9 mmol), was added to a solution of R/S-4-amino-6-bromo-3,4-dihydro-2,2-dimethyl-2H-1-benzopyran (0.4 g, 1.6 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried (60%). mp: 173.5-174.5° C., IR (KBr): υ: 3239 (N—H), 3088, 3041 (C—H aromatic), 2984, 2933 (C—H aliphatic), 1197 (C=S) cm$^{-1}$, Anal. ($C_{18}H_{18}N_2OSClBr$) C, H, N, S.

EXAMPLE 19

R/S-3,4-Dihydro-2,2-dimethyl-6-fluoro-4-(2-methoxyphenylaminothiocarbonylamino)-2H-1-benzopyran 2-Methoxyphenyl isothiocyanate (0.32 mL, 2.4 mmol) was added to a solution of R/S-4-amino-3,4-dihydro-2,2-dimethyl-6-fluoro-2H-1-benzopyran (0.4 g, 2 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried (40%). mp: 132-134° C., IR (KBr): υ: 3246 (N—H), 3029 (C—H aromatic), 2978, 2924 (C—H aliphatic), 1254 (CH$_3$—O—R), 1196 (C=S) cm$^{-1}$, Anal. (C$_{19}$H$_{21}$N$_2$O$_2$SF) C, H, N, S.

EXAMPLE 20

R/S-6-Chloro-3,4-dihydro-2,2-dimethyl-4-(2-methoxyphenylaminothiocarbonylamino)-2H-1-benzopyran 2-Methoxyphenyl isothiocyanate (0.31 mL, 2.3 mmol) was added to a solution of R/S-4-amino-6-chloro-3,4-dihydro-2,2-dimethyl-2H-1-benzopyran (0.4 g, 1.9 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried (54%). mp: 140-141° C., IR (KBr): υ: 3369, 3181 (N—H), 2976, 2951 (C—H aliphatic), 1260 (CH$_3$—O—R), 1195 (C=S) cm$^{-1}$, Anal. (C$_{19}$H$_{21}$N$_2$O$_2$SCl) C, H, N, S.

EXAMPLE 21

R/S-6-Bromo-3,4-dihydro-2,2-dimethyl-4-(2-methoxyphenylaminothiocarbonylamino)-2H-1-benzopyran 2-Methoxyphenyl isothiocyanate (0.26 mL, 1.9 mmol) was added to a solution of R/S-4-amino-6-bromo-3,4-dihydro-2,2-dimethyl-2H-1-benzopyran (0.4 g, 1.6 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried (63%). mp: 154-155° C., IR (KBr): υ: 3364, 3185 (N—H), 2976, 2950 (C—H aliphatic), 1258 (CH$_3$—O—R), 1195 (C=S) cm$^{-1}$, Anal. (C$_{19}$H$_{21}$N$_2$O$_2$SBr) C, H, N, S.

EXAMPLE 22

R/S-3,4-Dihydro-2,2-dimethyl-6-fluoro-4-(3-methoxyphenylaminothiocarbonylamino)-2H-1-benzopyran 3-Methoxyphenyl isothiocyanate (0.34 mL, 2.4 mmol) was added to a solution of R/S-4-amino-3,4-dihydro-2,2-dimethyl-6-fluoro-2H-1-benzopyran (0.4 g, 2 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried (48%). mp: 147-148.5° C., IR (KBr): υ: 3181 (N—H), 3028 (C—H aromatic), 2978, 2926 (C—H aliphatic), 1260 (CH$_3$—O—R), 1194 (C=S) cm$^{-1}$, Anal. (C$_{19}$H$_{21}$N$_2$O$_2$SF) C, H, N, S.

EXAMPLE 23

R/S-6-Chloro-3,4-dihydro-2,2-dimethyl-4-(3-methoxyphenylaminothiocarbonylamino)-2H-1-benzopyran 3-Methoxyphenyl isothiocyanate (0.32 mL, 2.3 mmol) was added to a solution of R/S-4-amino-6-chloro-3,4-dihydro-2,2-dimethyl-2H-1-benzopyran (0.4 g, 1.9 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried (56%). mp: 152-154° C., IR (KBr): υ: 3308, 3167 (N—H), 2976, 2930 (C—H aliphatic), 1262 (CH$_3$—O—R), 1201 (C=S) cm$^{-1}$, Anal. (C$_{19}$H$_{21}$N$_2$O$_2$SCl) C, H, N, S.

EXAMPLE 24

R/S-6-Bromo-3,4-dihydro-2,2-dimethyl-4-(3-methoxyphenylaminothiocarbonylamino)-2H-1-benzopyran 3-Methoxyphenyl isothiocyanate (0.27 mL, 1.9 mmol) was added to a solution of R/S-4-amino-6-bromo-3,4-dihydro-2,2-dimethyl-2H-1-benzopyran (0.4 g, 1.6 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried (61%). mp: 157-158° C., IR (KBr): υ: 3309, 3166 (N—H), 2974, 2930 (C—H aliphatic), 1262 (CH$_3$—O—R), 1201 (C=S) cm$^{-1}$, Anal. (C$_{19}$H$_{21}$N$_2$O$_2$SBr) C, H, N, S.

EXAMPLE 25

R/S-3,4-Dihydro-2,2-dimethyl-6-fluoro-4-(4-methoxyphenylaminothiocarbonylamino)-2H-1-benzopyran 4-Methoxyphenyl isothiocyanate (0.32 mL, 2.4 mmol) was added to a solution of R/S-4-amino-3,4-dihydro-2,2-dimethyl-6-fluoro-2H-1-benzopyran (0.4 g, 2 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried (51%). mp: 158-159.5° C., IR (KBr): υ: 3182 (N—H), 3031 (C—H aromatic), 2972, 2930 (C—H aliphatic), 1253 (CH$_3$—O—R), 1196 (C=S) cm$^{-1}$, Anal. (C$_{19}$H$_{21}$N$_2$O$_2$SF) C, H, N, S.

EXAMPLE 26

R/S-6-Chloro-3,4-dihydro-2,2-dimethyl-4-(4-methoxyphenylaminothiocarbonylamino)-2H-1-benzopyran 4-Methoxyphenyl isothiocyanate (0.31 mL, 2.3 mmol) was added to a solution of R/S-4-amino-6-chloro-3,4-dihydro-2, 2-dimethyl-2H-1-benzopyran (0.4 g, 1.9 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried (48%). mp: 158-160° C., IR (KBr): υ: 3192 (N—H), 3036 (C—H aromatic), 2974, 2929 (C—H aliphatic), 1249 (CH$_3$—O—R), 1199 (C=S) cm$^{-1}$, Anal. (C$_{19}$H$_{21}$N$_2$O$_2$SCl) C, H, N, S.

EXAMPLE 27

R/S-6-Bromo-3,4-dihydro-2,2-dimethyl-4-(4-methoxyphenylaminothiocarbonylamino)-2H-1-benzopyran 4-Methoxyphenyl isothiocyanate (0.26 mL, 1.9 mmol) was added to a solution of R/S-4-amino-6-bromo-3,4-dihydro-2,2-dimethyl-2H-1-benzopyran (0.4 g, 1.6 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried (51%). mp: 153.5-155° C., IR (KBr): υ: 3239 (N—H), 3039 (C—H aromatic), 2975, 2924 (C—H aliphatic), 1251 (CH$_3$—O—R), 1195 (C=S) cm$^{-1}$, Anal. (C$_{19}$H$_{21}$N$_2$O$_2$SBr) C, H, N, S.

EXAMPLE 28

R/S-4-(3-Cyanophenylaminothiocarbonylamino)-3,4-dihydro-2,2-dimethyl-6-fluoro-2H-1-benzopyran 3-Cyanophenyl isothiocyanate (0.38 g, 2.4 mmol) was added to a solution of R/S-4-amino-3,4-dihydro-2,2-dimethyl-6-fluoro-2H-1-benzopyran (0.4 g, 2 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried. The product was recrystallised in methanol:water (1:3) (28%). mp: 168-169° C., IR (KBr): υ: 3227 (N—H), 3041 (C—H aromatic), 2980, 2927 (C—H aliphatic), 2236 (C≡N), 1199 (C=S) cm$^{-1}$, Anal. (C$_{19}$H$_{18}$N$_3$OSF) C, H, N, S.

EXAMPLE 29

R/S-6-Chloro-4-(3-cyanophenylaminothiocarbonylamino)-3,4-dihydro-2,2-dimethyl-2H-1-benzopyran 3-Cyanophenyl isothiocyanate (0.36 g, 2.3 mmol) was added to a solution of R/S-4-amino-6-chloro-3,4-dihydro-2,2-dimethyl-2H-1-benzopyran (0.4 g, 1.9 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried (63%). mp: 185-186° C., IR (KBr): υ: 3338, 3275, 3212 (N—H), 3056 (C—H aromatic), 2976, 2932 (C—H aliphatic), 2237 (C≡N), 1202 (C=S) cm$^{-1}$, Anal. (C$_{19}$H$_{18}$N$_3$OSCl) C, H, N, S.

EXAMPLE 30

R/S-6-Bromo-4-(3-cyanophenylaminothiocarbonylamino)-3,4-dihydro-2,2-dimethyl-2H-1-benzopyran 3-Cyanophenyl isothiocyanate (0.30 g, 1.9 mmol) was added to a solution of R/S-4-amino-6-bromo-3,4-dihydro-2,2-dimethyl-2H-1-benzopyran (0.4 g, 1.6 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried (53%). mp: 181-182° C., IR (KBr): υ: 3329, 3162 (N—H), 3006 (C—H aromatic), 2984, 2930 (C—H aliphatic), 2230 (C≡N), 1200 (C=S) cm$^{-1}$, Anal. (C$_{19}$H$_{18}$N$_3$OSBr) C, H, N, S.

EXAMPLE 31

R/S-4-(4-Cyanophenylaminothiocarbonylamino)-3,4-dihydro-2,2-dimethyl-6-fluoro-2H-1-benzopyran 4-Cyanophenyl isothiocyanate (0.38 g, 2.4 mmol) was added to a solution of R/S-4-amino-3,4-dihydro-2,2-dimethyl-6-fluoro-2H-1-benzopyran (0.4 g, 2 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried (47%). mp: 202-202.5° C., IR (KBr): υ: 3248 (N—H), 3096, 3055 (C—H aromatic), 2989, 2974, 2950, 2933 (C—H aliphatic), 2227 (C≡N), 1197 (C=S) cm$^{-1}$, Anal. (C$_{19}$H$_{18}$N$_3$OSF) C, H, N, S.

EXAMPLE 32

R/S-6-Chloro-4-(4-cyanophenylaminothiocarbonylamino)-3,4-dihydro-2,2-dimethyl-2H-1-benzopyran 4-Cyanophenyl isothiocyanate (0.37 g, 2.3 mmol) was added to a solution of R/S-4-amino-6-chloro-3,4-dihydro-2,2-dimethyl-2H-1-benzopyran (0.4 g, 1.9 mmol) in methylene chloride (5 mL). After 30 minutes, the resulting precipitate was collected by filtration and petroleum ether was added and dried. The crude product was triturated with ethyl acetate. The insoluble was collected by filtration and petroleum ether was added to the filtrate. The resulting precipitate was collected by filtration, washed with petroleum ether and dried (63%). mp: 216° C., IR (KBr): υ: 3243 (N—H), 3092, 3039 (C—H aromatic), 2989, 2974, 2954, 2933 (C—H aliphatic), 2226 (C≡N), 1197 (C=S) cm$^{-1}$, Anal. (C$_{19}$H$_{18}$N$_3$OSCl) C, H, N, S.

EXAMPLE 33

R/S-6-Bromo-4-(4-cyanophenylaminothiocarbonylamino)-3,4-dihydro-2,2-dimethyl-2H-1-benzopyran 4-Cyanophenyl isothiocyanate (0.30 g, 1.9 mmol) was added to a solution of R/S-4-amino-6-bromo-3,4-dihydro-2,2-dimethyl-2H-1-benzopyran (0.4 g, 1.6 mmol) in methylene chloride (5 mL). After 30 minutes, the resulting precipitate was collected by filtration, washed with petroleum ether and dried (77%). mp: 207-208° C., IR (KBr): υ: 3248 (N—H), 3035 (C—H aromatic), 2988, 2934 (C—H aliphatic), 2226 (C≡N), 1197 (C=S) cm$^{-1}$, Anal. ($C_{19}H_{18}N_3OSBr$) C, H, N, S.

EXAMPLE 34

R/S-3,4-Dihydro-2,2-dimethyl-6-fluoro-4-(3-nitrophenylaminothiocarbonylamino)-2H-1-benzopyran 3-Nitrophenyl isothiocyanate (0.43 g, 2.4 mmol) was added to a solution of R/S-4-amino-3,4-dihydro-2,2-dimethyl-6-fluoro-2H-1-benzopyran (0.4 g, 2 mmol) in methylene chloride (5 mL). After 30 minutes, the resulting precipitate was collected by filtration, washed with petroleum ether and dried. The crude product was triturated with ethyl acetate. The insoluble was collected by filtration and petroleum ether was added to the filtrate. The resulting precipitate was collected by filtration, washed with petroleum ether and dried (47%). mp: 175-175.5° C., IR (KBr): υ: 3244 (N—H), 3098, 3035 (C—H aromatic), 2976, 2930 (C—H aliphatic), 1528, 1350 (N=O), 1197 (C=S) cm$^{-1}$, Anal. ($C_{18}H_{18}N_3O_3SF$) C, H, N, S.

EXAMPLE 35

R/S-6-Chloro-3,4-dihydro-2,2-dimethyl-4-(3-nitrophenylaminothiocarbonylamino)-2H-1-benzopyran 3-Nitrophenyl isothiocyanate (0.41 g, 2.3 mmol) was added to a solution of R/S-4-amino-6-chloro-3,4-dihydro-2,2-dimethyl-2H-1-benzopyran (0.4 g, 1.9 mmol) in methylene chloride (5 mL). After 30 minutes, the resulting precipitate was collected by filtration, washed with petroleum ether and dried (81%). mp: 188-188.5° C., IR (KBr): υ: 3183 (N—H), 3097, 3024 (C—H aromatic), 2980, 2928, 2950 (C—H aliphatic), 1530, 1345 (N=O), 1198 (C=S) cm$^{-1}$, Anal. ($C_{18}H_{18}N_3O_3SCl$) C, H, N, S.

EXAMPLE 36

R/S-6-Bromo-3,4-dihydro-2,2-dimethyl-4-(3-nitrophenylaminothiocarbonylamino)-2H-1-benzopyran 3-Nitrophenyl isothiocyanate (0.34 g, 1.9 mmol) was added to a solution of R/S-4-amino-6-bromo-3,4-dihydro-2,2-dimethyl-2H-1-benzopyran (0.4 g, 1.6 mmol) in methylene chloride (5 mL). After 30 minutes, the resulting precipitate was collected by filtration, washed with petroleum ether and dried (94%). mp: 186-187.5° C., IR (KBr): υ: 3227 (N—H), 3092, 3026 (C—H aromatic), 2981, 2926, 2949 (C—H aliphatic), 1530, 1349 (N=O), 1198 (C=S) cm$^{-1}$, Anal. ($C_{18}H_{18}N_3O_3SBr$) C, H, N, S.

EXAMPLE 37

R/S-3,4-Dihydro-2,2-dimethyl-6-fluoro-4-(4-nitrophenylaminothiocarbonylamino)-2H-1-benzopyran 4-Nitrophenyl isothiocyanate (0.43 g, 2.4 mmol) was added to a solution of R/S-4-amino-3,4-dihydro-2,2-dimethyl-6-fluoro-2H-1-benzopyran (0.4 g, 2 mmol) in methylene chloride (5 mL). After 30 minutes, the resulting precipitate was collected by filtration, washed with petroleum ether and dried (73%). mp: 192-194° C., IR (KBr): υ: 3221 (N—H), 3040 (C—H aromatic), 2980, 2933 (C—H aliphatic), 1522, 1346 (N=O), 1196 (C=S) cm$^{-1}$, Anal. ($C_{18}H_{18}N_3O_3SF$) C, H, N, S.

EXAMPLE 38

R/S-6-Chloro-3,4-dihydro-2,2-dimethyl-4-(4-nitrophenylaminothiocarbonylamino)-2H-1-benzopyran 4-Nitrophenyl isothiocyanate (0.40 g, 2.3 mmol) was added to a solution of R/S-4-amino-6-chloro-3,4-dihydro-2,2-dimethyl-2H-1-benzopyran (0.4 g, 1.9 mmol) in methylene chloride (5 mL). After 30 minutes, the resulting precipitate was collected by filtration, washed with petroleum ether and dried (84%). mp: 194-196° C., IR (KBr): υ: 3226 (N—H), 3059 (C—H aromatic), 2986, 2932 (C—H aliphatic), 1518, 1335 (N=O), 1198 (C=S) cm$^{-1}$, Anal. ($C_{18}H_{18}N_3O_3SCl$) C, H, N, S.

EXAMPLE 39

R/S-6-Bromo-3,4-dihydro-2,2-dimethyl-4-(4-nitrophenylaminothiocarbonylamino)-2H-1-benzopyran 4-Nitrophenyl isothiocyanate (0.34 g, 1.9 mmol) was added to a solution of R/S-4-amino-6-bromo-3,4-dihydro-2,2-dimethyl-2H-1-benzopyran (0.4 g, 1.6 mmol) in methylene chloride (5 mL). After 30 minutes, the resulting precipitate was collected by filtration, washed with petroleum ether and dried (80%). mp: 201-201.5° C., IR (KBr): υ: 3246 (N—H), 3050 (C—H aromatic), 2986, 2932 (C—H aliphatic), 1518, 1334 (N=O), 1199 (C=S) cm$^{-1}$, Anal. ($C_{18}H_{18}N_3O_3SBr$) C, H, N, S.

EXAMPLE 40

R/S-3,4-Dihydro-2,2-dimethyl-6-fluoro-4-(3-pyridylaminothiocarbonylamino)-2H-1-benzopyran 3-Pyridyl isothiocyanate (0.27 mL, 2.4 mmol) was added to a solution of R/S-4-amino-3,4-dihydro-2,2-dimethyl-6-fluoro-2H-1-benzopyran (0.4 g, 2 mmol) in methylene chloride (5 mL). After 30 minutes, the solvent was removed under vacuum and the crude product was triturated with methanol. The insoluble was collected by filtration and water was added to the filtrate. The resulting precipitate was collected by filtration, washed with water and dried (56%). mp: 161-162° C., IR (KBr): υ: 3174 (N—H), 2989 (C—H aliphatic), 1197 (C=S) cm$^{-1}$, Anal. ($C_{17}H_{18}N_3OSF$) C, H, N, S.

EXAMPLE 41

R/S-6-Chloro-3,4-dihydro-2,2-dimethyl-4-(3-pyridylaminothiocarbonylamino)-2H-1-benzopyran 3-Pyridyl isothiocyanate (0.26 mL, 2.3 mmol) was added to a solution of R/S-4-amino-6-chloro-3,4-dihydro-2,2-dimethyl-2H-1-benzopyran (0.4 g, 1.9 mmol) in methylene chloride (5 mL). After 30 minutes, the solvent was removed under vacuum and the crude product was triturated with methanol. The insoluble was collected by filtration and water was added to the filtrate. The resulting precipitate was collected by filtration, washed with water and dried (76%). mp: 144-144.5°

C., IR (KBr): υ: 3166 (N—H), 2986 (C—H aliphatic), 1198 (C—S) cm$^{-1}$, Anal. (C$_{17}$H$_{18}$N$_3$OSCl) C, H, N, S.

EXAMPLE 42

R/S-6-Bromo-3,4-dihydro-2,2-dimethyl-4-(3-pyridylaminothiocarbonylamino)-2H-1-benzopyran 3-Pyridyl isothiocyanate (0.21 mL, 1.9 mmol) was added to a solution of R/S-4-amino-6-bromo-3,4-dihydro-2,2-dimethyl-2H-1-benzopyran (0.4 g, 1.6 mmol) in methylene chloride (5 mL). After 30 minutes, the solvent was removed under vacuum and the crude product was triturated with methanol. The insoluble was collected by filtration and water was added to the filtrate. The resulting precipitate was collected by filtration, washed with water and dried (72%). mp: 146-148° C., IR (KBr): υ: 3183 (N—H), 3033 (C—H aromatic), 2975, 2923 (C—H aliphatic), 1198 (C=S) cm$^{-1}$, Anal. (C$_{17}$H$_{18}$N$_3$OSBr) C, H, N, S.

EXAMPLE 43

R/S-6-Chloro-3,4-dihydro-2,2-dimethyl-4-(3-thienylaminothiocarbonylamino)-2H-1-benzopyran 3-Thienyl isothiocyanate (0.32 g, 2.3 mmol) was added to a solution of R/S-4-amino-6-chloro-3,4-dihydro-2,2-dimethyl-2H-1-benzopyran (0.4 g, 1.9 mmol) in methylene chloride (5 mL). After 30 minutes, the resulting precipitate was collected by filtration, washed with methylene chloride and dried (69%). mp: 196-196.5° C., IR (KBr): υ: 3340, 3160 (N—H), 3087 (C—H aromatic), 2978, 2933 (C—H aliphatic), 1199 (C=S) cm$^{-1}$, Anal. (C$_{16}$H$_{17}$ClN$_2$OS$_2$) C, H, N, S.

EXAMPLE 44

R/S-6-Bromo-3,4-dihydro-2,2-dimethyl-4-(3-thienylaminothiocarbonyl-amino)-2H-1-benzopyran 3-Thienyl isothiocyanate (0.28 g, 1.9 mmol) was added to a solution of R/S-4-amino-6-bromo-3,4-dihydro-2,2-diethyl-2H-1-benzopyran (0.4 g, 1.6 mmol) in methylene chloride (5 mL). After 30 minutes, the solvent was removed under vacuum and the crude product was triturated with ethyl acetate. The insoluble was collected by filtration and hexane was added to the filtrate. The resulting precipitate was collected by filtration, washed with hexane and dried (65%). mp 181-182° C., IR (KBr): υ: 3331, 3161 (N—H), 2971, 2930 (C—H aliphatic), 1198 (C=S) cm$^{-1}$, Anal. (C$_{16}$H$_{17}$BrN$_2$OS$_2$) C, H, N, S.

EXAMPLE 45

R/S-6-Bromo-3,4-dihydro-2,2-dimethyl-4-(2-thienylaminothiocarbonylamino)-2H-1-benzopyran (6-Bromo-3,4-dihydro-2,2-dimethyl-2H-1-benzopyran)-4-yl isothiocyanate (1.26 g, 4.2 mmol) was added to a solution of 2-aminothiophene (0.35 g, 3.5 mmol) in methylene chloride (5 mL). The mixture was refluxed for 2 hours. The solvent was removed under vacuum and the crude product was triturated with methanol. The solution was treated with charcoal, filtered and water was added to the filtrate. The resulting precipitate was collected by filtration, washed with water and dried. The product was triturated with ethyl acetate. The insoluble was collected by filtration and hexane was added to the filtrate. The resulting precipitate was collected by filtration, washed with hexane and dried (10%). mp: 182-183° C., IR (KBr): υ: 3325, 3145 (N—H), 2926 (C—H aliphatic), 1198 (C=S) cm$^{-1}$, Anal. (C$_{16}$H$_{17}$BrN$_2$OS$_2$) C, H, N, S.

EXAMPLE 46

R/S-6-Bromo-3,4-dihydro-2,2-diethyl-4-(3-iodophenylaminothiocarbonylamino)-2H-1-benzopyran 3-Iodoaniline (0.15 mL, 1.2 mmol) was added to a solution of (6-bromo-3,4-dihydro-2,2-dimethyl-2H-1-benzopyran)-4-yl isothiocyanate (0.44 g, 1.5 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried (36%). mp: 185-186° C., IR (KBr): υ: 3322, 3130 (N—H), 2972 (C—H aliphatic), 1195 (C=S) cm$^{-1}$, Anal. (C$_{18}$H$_{18}$BrIN$_2$OS) C, H, N, S.

EXAMPLE 47

R/S-7-Chloro-4-(4-chlorophenylaminothiocarbonylamino)-3,4-dihydro-2,2-dimethyl-2H-1-benzopyran 3-Chlorophenyl acetate 3-Chlorophenol (100 g, 0.78 mol) was dissolved in acetic anhydride (75 mL, 0.8 mol). Upon addition of 1 drop of concentrated sulfuric acid, the temperature raised to 120° C. After 45 minutes, the mixture was cooled and poured into a solution of sodium hydrogenocarbonate (8 g in 1 L of water) and extracted with diethylether. The organic layer was washed with a saturated sodium hydrogenocarbonate solution, dried over magnesium sulfate and evaporated under reduced pressure. The resulting oil was used directly in the next step (84%). IR (KBr): υ: 3072 (C—H aromatic), 2939 (C—H aliphatic), 1773 (C=O), 1196 (C—O) cm$^{-1}$.

4-Chloro-2-hydroxyacetophenone

3-Chlorophenyl acetate (10 g, 0.0588 mol) was heated together with aluminum chloride (13.86 g, 0.105 mol) at 160° C. for 2 hours. The mixture was poured on water and extracted with diethylether. The organic layer was dried over magnesium sulfate and evaporated under reduced pressure. The residue was dissolved in methanol. The solution was treated with charcoal, filtered and water was added to the filtrate. The resulting oil was extracted with diethylether. The organic layer was dried over magnesium sulfate and diethylether was evaporated under reduced pressure. The resulting oil was used without further purification (77%). IR (KBr): υ: 3436 (O—H), 3073 (C—H aromatic), 1643 (C=O) cm$^{-1}$.

7-Chloro-3,4-dihydro-2,2-dimethyl-2H-1-benzopyran-4-one

A solution of 4-chloro-2-hydroxyacetophenone (20 g, 0.1176 mol), acetone (13.3 mL, 0.1811 mol) and pyrrolidine (15 mL, 0.18 mol) in methanol (475 mL) was stirred at 25° C. overnight. The mixture was then concentrated to a red oil. Water was added and the solution was adjusted to pH 1 with concentrated hydrochloric acid. The product was extracted with diethylether. The organic layer was dried over magnesium sulfate and diethylether was evaporated under reduced pressure. The residue was dissolved in a small volume of methanol. The solution was treated with charcoal, filtered and water was added to the filtrate. The resulting precipitate was collected by filtration, washed with water and dried (79%). mp: 63-66° C., IR (KBr): υ: 3086 (C—H aromatic), 2976, 2931 (C—H aliphatic), 1693 (C=0) cm$^{-1}$, Anal. ($C_{11}H_{11}O_2Cl$) C, H.

R/S-7-Chloro-3,4-dihydro-2,2-dimethyl-2H-1-benzopyran-4-ol

Sodium borohydride (3.3 g, 0.0873 mol) was added to a stirred suspension of 7-chloro-3,4-dihydro-2,2-dimethyl-2H-1-benzopyran-4-one (17 g, 0.0809 mol) in methanol (230 mL) at 0° C. and the mixture was maintained at this temperature for a further 30 minutes. After stirring for an additional 30 minutes at room temperature, concentrated hydrochloric acid was added until acid and the solvent was evaporated under reduced pressure. Water was added to the residue and the product was extracted with ethyl acetate. The organic layer was dried over magnesium sulfate and evaporated under reduced pressure. The resulting oil was dissolved in methanol. The solution was treated with charcoal, filtered and water was added to the filtrate. The resulting oil was extracted with diethylether. The organic layer was dried over magnesium sulfate and diethylether was evaporated under reduced pressure. The resulting oil was used without further purification (75%). IR (KBr): υ: 3436 (O—H), 3068 (C—H aromatic), 2978, 2931 (C—H aliphatic) cm$^{-1}$.

R/S-4-(N-Acetylamino)-7-chloro-3,4-dihydro-2,2-dimethyl-2H-1-benzopyran

A suspension of R/S-7-Chloro-3,4-dihydro-2,2-dimethyl-2H-1-benzopyran-4-ol (12 g, 0.0566 mol) in acetonitrile (140 mL) was added dropwise to a stirred mixture of acetonitrile (28 mL) and 98% sulphuric acid (7 mL) cooled in an ice/salt bath. Stirring was continued for 1 h at room temperature. The solution was poured into cold water and the precipitate collected by filtration, washed with water and dried (82%). mp: 143-146° C., IR (KBr): 3284 (N—H), 3074 (C—H aromatic), 2972, 2950, 2928 (C—H aliphatic), 1644 (C=O) cm$^{-1}$, Anal. ($C_{13}H_{16}NO_2Cl$) C, H, N.

R/S-4-Amino-7-chloro-3,4-dihydro-2,2-dimethyl-2H-1-benzopyran

A suspension of R/S-4-(N-acetylamino)-7-chloro-3,4-dihydro-2,2-dimethyl-2H-1-benzopyran (10.5 g, 41 mmol) was refluxed overnight in concentrated hydrochloric acid (420 mL). Hydrochloric acid was removed under reduced pressure and the residue was dissolved in hot water (130 mL). The solution was filtered and 10% aqueous sodium hydroxide was added to the filtrate until alkaline. The amine, which precipitated, was collected by filtration, washed with water and dried under vacuum. This product was used directly in the next step (9%). mp: 55-57° C.

IR (KBr): 3362 (N—H), 2975, 2932 (C—H aliphatic) cm$^{-1}$.

4-Chlorophenyl isothiocyanate (0.38 g, 2.3 mmol) was added to a solution of R/S-4-amino-7-chloro-3,4-dihydro-2,2-dimethyl-2H-1-benzopyran (0.4 g, 1.9 mmol) in methylene chloride (5 mL). After 30 minutes, the resulting precipitate was collected by filtration, washed with petroleum ether 40/60 and dried. The crude product was triturated with methanol. The insoluble was collected by filtration and water was added to the filtrate. The resulting precipitate was collected by filtration, washed with water and dried (63%). mp: 206.5-207.5° C., IR (KBr): υ: 3225 (N—H), 3097, 3048 (C—H aromatic), 2976, 2928 (C—H aliphatic), 1197 (C=S) cm$^{-1}$, Anal. ($C_{18}H_{18}N_2OSCl_2$) C, H, N, S.

EXAMPLE 48

R/S-7-Chloro-3,4-dihydro-2,2-dimethyl-4-(3-pyridylaminothiocarbonylamino)-2H-1-benzopyran 3-Pyridyl isothiocyanate (0.25 mL, 2.3 mmol) was added to a solution of R/S-4-amino-7-chloro-3,4-dihydro-2,2-dimethyl-2H-1-benzopyran (0.4 g, 1.9 mmol) in methylene chloride (5 mL). After 30 minutes, the solvent was removed under vacuum and the crude product was triturated with methanol. The insoluble was collected by filtration and water was added to the filtrate. The resulting precipitate was collected by filtration, washed with water and dried (73%). mp: 166-167° C., IR (KBr): υ: 3251, 3193 (N—H), 3038 (C—H aromatic), 2969, 2948, 2906 (C—H aliphatic), 1199 (C=S) cm$^{-1}$, Anal. ($C_{17}H_{18}N_3OSCl$) C, H, N, S.

EXAMPLE 49

R/S-7-Chloro-4-(3-cyanophenylaminothiocarbonylamino)-3,4-dihydro-2,2-dimethyl-2H-1-benzopyran 3-Cyanophenyl isothiocyanate (0.36 g, 2.3 mmol) was added to a solution of R/S-4-amino-7-chloro-3,4-dihydro-2,2-dimethyl-2H-1-benzopyran (0.4 g, 1.9 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried (61%). mp: 152-153° C., IR (KBr): υ: 3256, 3140 (N—H), 3077 (C—H aromatic), 2976, 2926 (C—H aliphatic), 2233 (C≡N), 1200 (C=S) cm$^{-1}$, Anal. ($C_{19}H_{18}N_3OSCl$) C, H, N, S.

EXAMPLE 50

R/S-6-Bromo-4-(4-chlorophenylaminothiocarbonylamino)-3,4-dihydro-spiro[2H-1-benzopyran-2,1'-cyclopentane]

6-Bromo-3,4-dihydro-spiro[2H-1-benzopyran-2,1'-cyclopentan]-4-one

A solution of 5-bromo-2-hydroxyacetophenone (31.6 g, 0.1477 mol), cyclopentanone (26 mL, 0.2939 mol) and pyrrolidine (24 mL, 0.288 mol) in methanol (600 mL) was stirred at 25° C. overnight. The mixture was then concentrated to a red oil. Water was added and the solution was adjusted to pH 1 with concentrated hydrochloric acid. The product was extracted with diethylether. The organic layer was evaporated under reduced pressure. The residue was then dissolved in a small volume of methanol. The solution was treated with charcoal, filtered and water was added to the filtrate. The residue was extracted with diethylether. The organic layer was dried over magnesium sulfate and diethylether was evaporated under reduced pressure. The product was used directly in the next step (77%).

6-Bromo-3,4-dihydro-spiro[2H-1-benzopyran-2,1'-cyclopentan]-4-ol

Sodium borohydride (4.65 g, 0.123 mol) was added to a stirred suspension of 6-bromo-3,4-dihydro-spiro[2H-1-benzopyran-2,1'-cyclopentan]-4-one (31.83 g, 0.1137 mol) in methanol (650 mL) at 0° C. and the mixture was maintained at this temperature for a further 30 minutes. After stirring for an additional 30 minutes at room temperature, concentrated hydrochloric acid was added until acid and the solvent was evaporated under reduced pressure. Water was added to the residue and the product was extracted with ethyl acetate. The organic layer was dried over magnesium sulfate and evaporated under reduced pressure. The crude product was recrystallized from diethylether/petroleum ether 40-60° C. (⅓). The resulting precipitate was collected by filtration, washed with petroleum ether and dried (71%). mp: 123-123.5° C., IR (KBr): 3271 (O—H), 2963, 2873 (C—H aliphatic) cm$^{-1}$, Anal. ($C_{13}H_{15}O_2Br$) C, H.

R/S-4-(N-Acetylamino)-6-bromo-3,4-dihydro-spiro[2H-1-benzopyran-2,1'-cyclopentan]

A suspension of 6-bromo-3,4-dihydro-spiro[2H-1-benzopyran-2,1'-cyclopentan]-4-ol (23 g, 0.082 mol) in acetonitrile (900 mL) was added dropwise to a stirred mixture of acetonitrile (41 mL) and 98% sulphuric acid (10.5 mL) cooled in an ice/salt bath. Stirring was continued for 1 h at room temperature. The solution was poured into cold water and the precipitate collected by filtration, washed with water and dried (80%). mp: 170-171.5° C., IR (KBr): 3281 (N—H), 3072 (C—H aromatic), 2966, 2928, 2874 (C—H aliphatic), 1641 (C=O) cm$^{-1}$, Anal. ($C_{15}H_{18}NO_2Br$) C, H, N.

R/S-4-Amino-6-bromo-3,4-dihydro-spiro[2H-1-benzopyran-2,1'-cyclopentan]

A suspension of R/S-4-(N-acetylamino)-6-bromo-3,4-dihydro-spiro[2H-1-benzopyran-2,1'-cyclopentan] (5 g, 15 mmol) in concentrated hydrochloric acid (100 mL) was refluxed overnight. Hydrochloric acid was removed under vacuum and the residue was dissolved in hot water (50 mL). The solution was filtered and 10% aqueous sodium hydroxide solution was added to the filtrate until alkaline. The amine was collected by filtration, washed with water and dried under vacuum. This product was used without further purification. mp: 44.5-46° C., IR (KBr): 3363, 3292 (N—H), 3054 (C—H aromatic), 2950, 2910 (C—H aliphatic) cm$^{-1}$.

4-Chlorophenyl isothiocyanate (0.27 g, 1.7 mmol) was added to a solution of R/S-4-amino-6-bromo-3,4-dihydro-spiro[2H-1-benzopyran-2,1'-cyclopentane] (0.4 g, 1.4 mmol) in methylene chloride (5 mL). After 30 minutes, the solvent was removed under vacuum and the crude product was triturated with ethyl acetate. The insoluble was collected by filtration and petroleum ether was added to the filtrate. The resulting precipitate was collected by filtration, washed with petroleum ether and dried (29%). mp: 183-185° C., IR (KBr): υ: 3234 (N—H), 3035 (C—H aromatic), 2960, 2874 (C—H aliphatic), 1239 (C=S) cm$^{-1}$, Anal. ($C_{20}H_{20}N_2OClBrS$) C, H, N, S.

EXAMPLE 51

R/S-3,4-Dihydro-2,2-dimethyl-6-fluoro-4-(4-fluorophenylaminothiocarbonylamino)-2H-1-benzopyran 4-Fluorophenyl isothiocyanate (0.19 g, 1.2 mmol) was added to a solution of R/S-4-amino-3,4-dihydro-2,2-dimethyl-6-fluoro-2H-1-benzopyran (0.2 g, 1 mmol) in methylene chloride (4 mL). After 30 minutes, the solvent was removed under vacuum and the crude product was triturated petroleum ether. The resulting precipitate was collected by filtration, washed with petroleum ether and dried (68%). mp: 188° C., Anal. ($C_{18}H_{18}N_2OSF_2$) C, H, N, S.

EXAMPLE 52

R/S-4-(3,5-Dichlorophenylaminothiocarbonylamino)-3,4-dihydro-2,2-dimethyl-6-fluoro-2H-1-benzopyran 3,5-Dichlorophenyl isothiocyanate (0.25 g, 1.2 mmol) was added to a solution of R/S-4-amino-3,4-dihydro-2,2-dimethyl-6-fluoro-2H-1-benzopyran (0.2 g, 1 mmol) in methylene chloride (4 mL). After 30 minutes, the resulting precipitate was collected by filtration, washed with petroleum ether and dried. The product was recrystallised in methanol:water (1:3) and dried (55%). mp: 187° C., Anal. ($C_{18}H_{17}N_2OSFCl_2$) C, H, N, S.

EXAMPLE 53

R/S-4-(3,5-Difluorophenylaminothiocarbonylamino)-3,4-dihydro-2,2-dimethyl-6-fluoro-2H-1-benzopyran 3,5-Difluorophenyl isothiocyanate (0.2 mL, 1.54 mmol) was added to a solution of R/S-4-amino-3,4-dihydro-2,2-dimethyl-6-fluoro-2H-1-benzopyran (0.25 g, 1.28 mmol) in methylene chloride (3 mL). After 30 minutes, the resulting precipitate was collected by filtration, washed with petroleum ether and dried. The product was recrystallised in methanol:water (1:3) and dried (53%). mp: 182° C., Anal. ($C_{18}H_{17}N_2OSF_3$) C, H, N, S.

EXAMPLE 54

R/S-6-Bromo-3,4-dihydro-2,2-dimethyl-4-(4-trifluoromethylphenylaminothiocarbonylamino)-2H-1-benzopyran 4-Trifluoromethylphenyl isothiocyanate (0.29 g, 1.41 mmol) was added to a solution of R/S-4-amino-6-bromo-3,4-dihydro-2,2-dimethyl-2H-1-benzopyran (0.3 g, 1.18 mmol) in methylene chloride (3 mL). After 30 minutes, the resulting precipitate was collected by filtration, washed with petroleum ether 40/60 and dried. The product was triturated with ethyl acetate. The insoluble was collected by filtration and petroleum ether was added to the filtrate. The resulting precipitate was collected by filtration, washed with petroleum ether and dried (25%). mp: 182-183° C., Anal. ($C_{19}H_{18}N_2OSF_3Br$) C, H, N, S.

EXAMPLE 55

R/S-6-Bromo-3,4-dihydro-2,2-dimethyl-4-(3-trifluoromethylphenylaminothiocarbonylamino)-2H-1-benzopyran 4-Trifluoromethylphenyl isothiocyanate (0.21 mL, 1.41 mmol) was added to a solution of R/S-4-amino-6-bromo-3,4-dihydro-2,2-dimethyl-2H-1-benzopyran (0.3 g, 1.18 mmol) in methylene chloride (3 mL). After 30 minutes, the resulting precipitate was collected by filtration, washed with petroleum ether 40/60 and dried (65%). mp: 189° C., Anal. ($C_{19}H_{18}N_2OSF_3Br$) C, H, N, S.

EXAMPLE 56

R/S-3,4-Dihydro-2,2-dimethyl-6-fluoro-4-(2-methoxyphenylaminocarbonylamino)-2H-1-benzopyran 2-Methoxyphenyl isocyanate (0.32 mL, 2.4 mmol) was added to a solution of R/S-4-amino-3,4-dihydro-2,2-dimethyl-6-fluoro-2H-1-benzopyran (0.4 g, 2 mmol) in methylene chloride (5 mL). After 30 min at room temperature, the solvent was removed under reduced pressure and the crude product was triturated with ethyl acetate. The insoluble was eliminated by filtration and petroleum ether was added to the filtrate. The resulting precipitate was collected by filtration, washed with petroleum ether and dried. The product was then crystallized in a mixture of methanol/water. The resulting precipitate was collected by filtration, washed with water and dried. The crude product was triturated with ethyl acetate. The insoluble was eliminated by filtration and petroleum ether 40/60 was added to the filtrate. The resulting precipitate was collected by filtration, washed with petroleum ether 40/60 and dried (11%). mp: 172-175° C., IR (KBr): υ: 3334 (N—H), 2978, 2934, 2837 (C—H aliphatic), 1643 (C═O), 1253 ($CH_3$—O) $cm^{-1}$, Anal. ($C_{19}H_{21}N_2O_3F$) C, H, N.

EXAMPLE 57

R/S-6-Chloro-3,4-dihydro-2,2-dimethyl-4-(2-methoxyphenylaminocarbonylamino)-2H-1-benzopyran 2-Methoxyphenyl isocyanate (0.30 mL, 2.3 mmol) was added to a solution of R/S-4-amino-6-chloro-3,4-dihydro-2,2-dimethyl-2H-1-benzopyran (0.4 g, 1.9 mmol) in methylene chloride (5 mL). After 20 min at room temperature, the resulting precipitate was collected by filtration, washed with petroleum ether 40/60 and dried. The crude product was triturated with ethyl acetate. The insoluble was eliminated by filtration and petroleum ether 40/60 was added to the filtrate. The resulting precipitate was collected by filtration, washed with petroleum ether 40/60 and dried (60%). mp: 180-181° C., IR (KBr): υ: 3309 (N—H), 3063 (C—H aromatic), 2980, 2931, 2838 (C—H aliphatic), 1638 (C═O), 1257 ($CH_3$—O) $cm^{-1}$, Anal. ($C_{19}H_{21}N_2O_3Cl$) C, H, N.

EXAMPLE 58

R/S-6-Bromo-3,4-dihydro-2,2-dimethyl-4-(2-methoxyphenylaminocarbonylamino)-2H-1-benzopyran 2-Methoxyphenyl isocyanate (0.25 mL, 1.9 mmol) was added to a solution of R/S-4-amino-6-bromo-3,4-dihydro-2,2-dimethyl-2H-1-benzopyran (0.4 g, 1.6 mmol) in methylene chloride (5 mL). After 20 min at room temperature, the resulting precipitate was collected by filtration, washed with petroleum ether 40/60 and dried. The crude product was triturated with ethyl acetate. The insoluble was eliminated by filtration and petroleum ether 40/60 was added to the filtrate. The resulting precipitate was collected by filtration, washed with petroleum ether 40/60 and dried (58%). mp: 191-193° C., IR (KBr): υ: 3312 (N—H), 3062 (C—H aromatic), 2979, 2931, 2837 (C—H aliphatic), 1638 (C═O), 1256 ($CH_3$—O) $cm^{-1}$, Anal. ($C_{19}H_{21}N_2O_3Br$) C, H, N.

EXAMPLE 59

R/S-3,4-Dihydro-2,2-dimethyl-6-fluoro-4-(3-methoxyphenylaminocarbonylamino)-2H-1-benzopyran 3-Methoxyphenyl isocyanate (0.31 mL, 2.4 mmol) was added to a solution of R/S-4-amino-3,4-dihydro-2,2-dimethyl-6-fluoro-2H-1-benzopyran (0.4 g, 2 mmol) in methylene chloride (5 mL). After 20 min at room temperature, the resulting precipitate was collected by filtration, washed with petroleum ether 40/60 and dried. The crude product was triturated with ethyl acetate. The insoluble was eliminated by filtration and petroleum ether 40/60 was added to the filtrate. The resulting precipitate was collected by filtration, washed with petroleum ether 40/60 and dried. The product was then crystallized in a mixture of methanol/water. The resulting precipitate was collected by filtration, washed with water and dried. The crude product was dissolved in a minimum of hot methanol and the insoluble was eliminated by filtration. After cooling, the resulting precipitate was collected by filtration and dried (25%). mp: 189.5-190.5° C., IR (KBr): υ: 3300 (N—H), 3086 (C—H aromatic), 2983, 2946, 2835 (C—H aliphatic), 1642 (C═O), 1252 ($CH_3$—O) $cm^{-1}$, Anal. ($C_{19}H_{21}N_2O_3F$) C, H, N.

EXAMPLE 60

R/S-6-Chloro-3,4-dihydro-2,2-dimethyl-4-(3-methoxyphenylaminocarbonylamino)-2H-1-benzopyran 3-Methoxyphenyl isocyanate (0.30 mL, 2.3 mmol) was added to a solution of R/S-4-amino-6-chloro-3,4-dihydro-2,2-dimethyl-2H-1-benzopyran (0.4 g, 1.9 mmol) in methylene chloride (5 mL). After 20 min at room temperature, the resulting precipitate was collected by filtration, washed with petroleum ether 40/60 and dried. The crude product was triturated with ethyl acetate. The insoluble was eliminated by filtration and petroleum ether 40/60 was added to the filtrate. The resulting precipitate was collected by filtration, washed with petroleum ether 40/60 and dried (66%). mp: 164-167° C., IR (KBr): υ: 3346 (N—H), 2976, 2957, 2930 (C—H aliphatic), 1649 (C═O), 1261 ($CH_3$—O) $cm^{-1}$, Anal. ($C_{19}H_{21}N_2O_3Cl$) C, H, N.

EXAMPLE 61

R/S-6-Bromo-3,4-dihydro-2,2-dimethyl-4-(3-methoxyphenylaminocarbonylamino)-2H-1-benzopyran 3-Methoxyphenyl isocyanate (0.25 mL, 1.9 mmol) was added to a solution of R/S-4-amino-6-bromo-3,4-dihydro-2,2-dimethyl-2H-1-benzopyran (0.4 g, 1.6 mmol) in methylene chloride (5 mL). After 20 min at room temperature, the resulting precipitate was collected by filtration, washed with petroleum ether 40/60 and dried (84%). mp: 172-174° C., IR (KBr): υ: 3331 (N—H), 3089 (C—H aromatic), 2975, 2934, 2830 (C—H aliphatic), 1628 (C═O), 1257 ($CH_3$—O) $cm^{-1}$, Anal. ($C_{19}H_{21}N_2O_3Br$) C, H, N.

EXAMPLE 62

R/S-3,4-Dihydro-2,2-dimethyl-6-fluoro-4-(4-methoxyphenylaminocarbonylamino)-2H-1-benzopyran 4-Methoxyphenyl isocyanate (0.31 mL, 2.4 mmol) was added to a solution of R/S-4-amino-3,4-dihydro-2,2-dimethyl-6-fluoro-2H-1-benzopyran (0.4 g, 2 mmol) in methylene chloride (5 mL). After 20 min at room temperature, the resulting precipitate was collected by filtration, washed with petroleum ether 40/60 and dried. The crude product was triturated with ethyl acetate. The insoluble was eliminated by filtration and petroleum ether 40/60 was added to the filtrate. The resulting precipitate was collected by filtration, washed with petroleum ether 40/60 and dried (30%). mp: 158-177° C., IR (KBr): υ: 3327 (N—H), 2979, 2951, 2836 (C—H aliphatic), 1634 (C=O), 1244 (CH$_3$—O) cm$^{-1}$, Anal. (C$_{19}$H$_{21}$N$_2$O$_3$F) C, H, N.

EXAMPLE 63

R/S-6-Chloro-3,4-dihydro-2,2-dimethyl-4-(4-methoxyphenylaminocarbonylamino)-2H-1-benzopyran 4-Methoxyphenyl isocyanate (0.30 mL, 2.3 mmol) was added to a solution of R/S-4-amino-6-chloro-3,4-dihydro-2,2-dimethyl-2H-1-benzopyran (0.4 g, 1.9 mmol) in methylene chloride (5 mL). After 20 min at room temperature, the resulting precipitate was collected by filtration, washed with petroleum ether 40/60 and dried. The crude product was triturated with ethyl acetate. The insoluble was eliminated by filtration and petroleum ether 40/60 was added to the filtrate. The resulting precipitate was collected by filtration, washed with petroleum ether 40/60 and dried. The crude product was dissolved in a minimum of hot methanol and the insoluble was eliminated by filtration. After cooling, the resulting precipitate was collected by filtration and dried (51%). mp: 159-161° C., IR (KBr): υ: 3343 (N—H), 2976, 2932, 2829 (C—H aliphatic), 1634 (C=O), 1230 (CH$_3$—O) cm$^{-1}$, Anal. (C$_{19}$H$_{21}$N$_2$O$_3$Cl) C, H, N.

EXAMPLE 64

R/S-6-Bromo-3,4-dihydro-2,2-dimethyl-4-(4-methoxyphenylaminocarbonylamino)-2H-1-benzopyran 4-Methoxyphenyl isocyanate (0.25 mL, 1.9 mmol) was added to a solution of R/S-4-amino-6-bromo-3,4-dihydro-2,2-dimethyl-2H-1-benzopyran (0.4 g, 1.6 mmol) in methylene chloride (5 mL). After 20 min at room temperature, the resulting precipitate was collected by filtration, washed with petroleum ether 40/60 and dried. The crude product was triturated with ethyl acetate. The insoluble was eliminated by filtration and petroleum ether 40/60 was added to the filtrate. The resulting precipitate was collected by filtration, washed with petroleum ether 40/60 and dried. The crude product was dissolved in a minimum of hot methanol and the insoluble was eliminated by filtration. After cooling, the resulting precipitate was collected by filtration and dried (38%). mp: 182-185° C., IR (KBr): υ: 3321 (N—H), 2977, 2932, 2833 (C—H aliphatic), 1634 (C=O), 1230 (CH$_3$—O) cm$^{-1}$, Anal. (C$_{19}$H$_{21}$N$_2$O$_3$Br) C, H, N.

EXAMPLE 65

R/S-3,4-Dihydro-2,2-dimethyl-6-fluoro-4-(2-methylphenylaminocarbonylamino)-2H-1-benzopyran 2-Methylphenyl isocyanate (0.31 mL, 2.4 mmol) was added to a solution of R/S-4-amino-3,4-dihydro-2,2-dimethyl-6-fluoro-2H-1-benzopyran (0.4 g, 2 mmol) in methylene chloride (5 mL). After 20 min at room temperature, the resulting precipitate was collected by filtration, washed with petroleum ether 40/60 and dried. The crude product was triturated with ethyl acetate. The insoluble was eliminated by filtration and petroleum ether 40/60 was added to the filtrate. The resulting precipitate was collected by filtration, washed with petroleum ether 40/60 and dried (75%). mp: 197-198° C., IR (KBr): υ: 3325 (N—H), 2978 (C—H aliphatic), 1634 (C=O) cm$^{-1}$, Anal. (C$_{19}$H$_{21}$N$_2$O$_2$F) C, H, N.

EXAMPLE 66

R/S-6-Chloro-3,4-dihydro-2,2-dimethyl-4-(2-methylphenylaminocarbonylamino)-2H-1-benzopyran 2-Methylphenyl isocyanate (0.28 mL, 2.3 mmol) was added to a solution of R/S-4-amino-6-chloro-3,4-dihydro-2,2-dimethyl-2H-1-benzopyran (0.4 g, 1.9 mmol) in methylene chloride (5 mL). After 20 min at room temperature, the resulting precipitate was collected by filtration, washed with petroleum ether 40/60 and dried. The crude product was triturated with ethyl acetate. The insoluble was eliminated by filtration and petroleum ether 40/60 was added to the filtrate. The resulting precipitate was collected by filtration, washed with petroleum ether 40/60 and dried (61%). mp: 190.5-191.5° C., IR (KBr): υ: 3314 (N—H), 2978, 2925 (C—H aliphatic), 1638 (C=O) cm$^{-1}$, Anal. (C$_{19}$H$_{21}$N$_2$O$_2$Cl) C, H, N.

EXAMPLE 67

R/S-6-Bromo-3,4-dihydro-2,2-dimethyl-4-(2-methylphenylaminocarbonylamino)-2H-1-benzopyran 2-Methylphenyl isocyanate (0.23 mL, 1.9 mmol) was added to a solution of R/S-4-amino-6-bromo-3,4-dihydro-2,2-dimethyl-2H-1-benzopyran (0.4 g, 1.6 mmol) in methylene chloride (5 mL). After 20 min at room temperature, the resulting precipitate was collected by filtration, washed with petroleum ether 40/60 and dried. The crude product was triturated with ethyl acetate. The insoluble was eliminated by filtration and petroleum ether 40/60 was added to the filtrate. The resulting precipitate was collected by filtration, washed with petroleum ether 40/60 and dried (70%). mp: 198-199° C., IR (KBr): υ: 3318 (N—H), 2977 (C—H aliphatic), 1638 (C=O) cm$^{-1}$, Anal. (C$_{19}$H$_{21}$N$_2$O$_2$Br) C, H, N.

EXAMPLE 68

R/S-3,4-Dihydro-2,2-dimethyl-6-fluoro-4-(3-methylphenylaminocarbonylamino)-2H-1-benzopyran 3-Methylphenyl isocyanate (0.31 mL, 2.4 mmol) was added to a solution of R/S-4-amino-3,4-dihydro-2,2-dimethyl-6-fluoro-2H-1-benzopyran (0.4 g, 2 mmol) in methylene chloride (5 mL). After 20 min at room temperature, the resulting precipitate was collected by filtration, washed with petroleum ether 40/60 and dried. The crude product was triturated with ethyl acetate. The insoluble was eliminated by filtration and petroleum ether 40/60 was added to the filtrate.

The resulting precipitate was collected by filtration, washed with petroleum ether 40/60 and dried (75%). mp: 193-194° C., IR (KBr): υ: 3327 (N—H), 2976, 2924 (C—H aliphatic), 1634 (C=O) cm$^{-1}$, Anal. ($C_{19}H_{21}N_2O_2F$) C, H, N.

EXAMPLE 69

R/S-6-Chloro-3,4-dihydro-2,2-dimethyl-4-(3-methylphenylaminocarbonylamino)-2H-1-benzopyran 3-Methylphenyl isocyanate (0.29 mL, 2.3 mmol) was added to a solution of R/S-4-amino-6-chloro-3,4-dihydro-2,2-dimethyl-2H-1-benzopyran (0.4 g, 1.9 mmol) in methylene chloride (5 mL). After 20 min at room temperature, the resulting precipitate was collected by filtration, washed with petroleum ether 40/60 and dried. The crude product was triturated with ethyl acetate. The insoluble was eliminated by filtration and petroleum ether 40/60 was added to the filtrate. The resulting precipitate was collected by filtration, washed with petroleum ether 40/60 and dried. The crude product was dissolved in a minimum of hot methanol and the insoluble was eliminated by filtration. After cooling, the resulting precipitate was collected by filtration and dried (22%). mp: 191-192° C., IR (KBr): υ: 3333 (N—H), 3048 (C—H aromatic), 2977, 2923 (C—H aliphatic), 1639 (C=O) cm$^{-1}$, Anal. ($C_{19}H_{21}N_2O_2Cl$) C, H, N.

EXAMPLE 70

R/S-6-Bromo-3,4-dihydro-2,2-dimethyl-4-(3-methylphenylaminocarbonylamino)-2H-1-benzopyran 3-Methylphenyl isocyanate (0.24 mL, 1.9 mmol) was added to a solution of R/S-4-amino-6-bromo-3,4-dihydro-2,2-dimethyl-2H-1-benzopyran (0.4 g, 1.6 mmol) in methylene chloride (5 mL). After 20 min at room temperature, the resulting precipitate was collected by filtration, washed with petroleum ether 40/60 and dried. The crude product was triturated with ethyl acetate. The insoluble was eliminated by filtration and petroleum ether 40/60 was added to the filtrate. The resulting precipitate was collected by filtration, washed with petroleum ether 40/60 and dried. The crude product was dissolved in a minimum of hot methanol and the insoluble was eliminated by filtration. After cooling, the resulting precipitate was collected by filtration and dried (33%). mp: 197-198° C., IR (KBr): υ: 3338 (N—H), 3046 (C—H aromatic), 2976, 2923 (C—H aliphatic), 1639 (C=O) cm$^{-1}$, Anal. ($C_{19}H_{21}N_2O_2Br$) C, H, N.

EXAMPLE 71

R/S-3,4-Dihydro-2,2-dimethyl-6-fluoro-4-(4-methylphenylaminocarbonylamino)-2H-1-benzopyran 4-Methylphenyl isocyanate (0.31 mL, 2.4 mmol) was added to a solution of R/S-4-amino-3,4-dihydro-2,2-dimethyl-6-fluoro-2H-1-benzopyran (0.4 g, 2 mmol) in methylene chloride (5 mL). After 20 min at room temperature, the resulting precipitate was collected by filtration, washed with petroleum ether 40/60 and dried (79%). mp: 185-186° C., IR (KBr): υ: 3370, 3297 (N—H), 2978, 2928 (C—H aliphatic), 1640 (C=O) cm$^{-1}$, Anal. ($C_{19}H_{21}N_2O_2F$) C, H, N.

EXAMPLE 72

R/S-6-Chloro-3,4-dihydro-2,2-dimethyl-4-(4-methylphenylaminocarbonylamino)-2H-1-benzopyran 4-Methylphenyl isocyanate (0.29 mL, 2.3 mmol) was added to a solution of R/S-4-amino-6-chloro-3,4-dihydro-2,2-dimethyl-2H-1-benzopyran (0.4 g, 1.9 mmol) in methylene chloride (5 mL). After 20 min at room temperature, the resulting precipitate was collected by filtration, washed with petroleum ether 40/60 and dried (84%). mp: 193-194° C., IR (KBr): υ: 3330 (N—H), 2978 (C—H aliphatic), 1636 (C=O) cm$^{-1}$, Anal. ($C_{19}H_{21}N_2O_2Cl$) C, H, N.

EXAMPLE 73

R/S-6-Bromo-3,4-dihydro-2,2-dimethyl-4-(4-methylphenylaminocarbonylamino)-2H-1-benzopyran 4-Methylphenyl isocyanate (0.24 mL, 1.9 mmol) was added to a solution of R/S-4-amino-6-bromo-3,4-dihydro-2,2-dimethyl-2H-1-benzopyran (0.4 g, 1.6 mmol) in methylene chloride (5 mL). After 20 min at room temperature, the resulting precipitate was collected by filtration, washed with petroleum ether 40/60 and dried (85%). mp: 192-193° C., IR (KBr): υ: 3327 (N—H), 2977 (C—H aliphatic), 1635 (C=O) cm$^{-1}$, Anal. ($C_{19}H_{21}N_2O_2Br$) C, H, N.

EXAMPLE 74

R/S-4-(2-Chlorophenylaminocarbonylamino)-3,4-dihydro-2,2-dimethyl-6-fluoro-2H-1-benzopyran 2-Chlorophenyl isocyanate (0.30 mL, 2.4 mmol) was added to a solution of R/S-4-amino-3,4-dihydro-2,2-dimethyl-6-fluoro-2H-1-benzopyran (0.4 g, 2 mmol) in methylene chloride (5 mL). After 20 min at room temperature, the resulting precipitate was collected by filtration, washed with petroleum ether 40/60 and dried. The crude product was triturated with ethyl acetate. The insoluble was eliminated by filtration and petroleum ether 40/60 was added to the filtrate. The resulting precipitate was collected by filtration, washed with petroleum ether 40/60 and dried (54%). mp: 181-183° C., IR (KBr): υ: 3337 (N—H), 2978 (C—H aliphatic), 1641 (C=O) cm$^{-1}$, Anal. ($C_{18}H_{18}N_2O_2FCl$) C, H, N.

EXAMPLE 75

R/S-6-Chloro-4-(2-chlorophenylaminocarbonylamino)-3,4-dihydro-2,2-dimethyl-2H-1-benzopyran 2-Chlorophenyl isocyanate (0.27 mL, 2.3 mmol) was added to a solution of R/S-4-amino-6-chloro-3,4-dihydro-2,2-dimethyl-2H-1-benzopyran (0.4 g, 1.9 mmol) in methylene chloride (5 mL). After 30 min at room temperature, the solvent was removed under reduced pressure and the crude product was triturated with ethyl acetate. The insoluble was eliminated by filtration and petroleum ether was added to the filtrate. The resulting precipitate was collected by filtration, washed with petroleum ether and dried (64%). mp: 195-195.5° C., IR (KBr): υ: 3402, 3275 (N—H), 2982, 2948 (C—H aliphatic), 1668 (C=O) cm$^{-1}$, Anal. ($C_{18}H_{18}N_2O_2Cl_2$) C, H, N.

EXAMPLE 76

R/S-6-Bromo-4-(2-chlorophenylaminocarbonylamino)-3,4-dihydro-2,2-dimethyl-2H-1-benzopyran 2-Chlorophenyl isocyanate (0.23 mL, 1.9 mmol) was added to a solution of R/S-4-amino-6-bromo-3,4-dihydro-2,2-dimethyl-2H-1-benzopyran (0.4 g, 1.6 mmol) in methylene chloride (5 mL). After 20 min at room temperature, the resulting precipitate was collected by filtration, washed with petroleum ether 40/60 and dried (60%). mp: 184-185.5° C., IR (KBr): υ: 3401, 3275 (N—H), 3085 (C—H aromatic), 2979, 2947, 2933 (C—H aliphatic), 1667 (C═O) cm$^{-1}$, Anal. ($C_{18}H_{18}N_2O_2BrCl$) C, H, N.

EXAMPLE 77

R/S-4-(3-Chlorophenylaminocarbonylamino)-3,4-dihydro-2,2-dimethyl-6-fluoro-2H-1-benzopyran 3-Chlorophenyl isocyanate (0.30 mL, 2.4 mmol) was added to a solution of R/S-4-amino-3,4-dihydro-2,2-dimethyl-6-fluoro-2H-1-benzopyran (0.4 g, 2 mmol) in methylene chloride (5 mL). After 20 min at room temperature, the resulting precipitate was collected by filtration, washed with petroleum ether 40/60 and dried. The crude product was triturated with ethyl acetate. The insoluble was eliminated by filtration and petroleum ether 40/60 was added to the filtrate. The resulting precipitate was collected by filtration, washed with petroleum ether 40/60 and dried (56%). mp: 214-215° C., IR (KBr): υ: 3325 (N—H), 2983 (C—H aliphatic), 1642 (C═O) cm$^{-1}$, Anal. ($C_{18}H_{18}N_2O_2FCl$) C, H, N.

EXAMPLE 78

R/S-6-Chloro-4-(3-chlorophenylaminocarbonylamino)-3,4-dihydro-2,2-dimethyl-2H-1-benzopyran 3-Chlorophenyl isocyanate (0.28 mL, 2.3 mmol) was added to a solution of R/S-4-amino-6-chloro-3,4-dihydro-2,2-dimethyl-2H-1-benzopyran (0.4 g, 1.9 mmol) in methylene chloride (5 mL). After 20 min at room temperature, the resulting precipitate was collected by filtration, washed with petroleum ether 40/60 and dried (89%). mp: 190-192° C.; IR (KBr): υ: 3324 (N—H), 2979 (C—H aliphatic), 1636 (C═O) cm$^{-1}$, Anal. ($C_{18}H_{18}N_2O_2Cl_2$) C, H, N.

EXAMPLE 79

R/S-6-Bromo-4-(3-chlorophenylaminocarbonylamino)-3,4-dihydro-2,2-dimethyl-2H-1-benzopyran 3-Chlorophenyl isocyanate (0.23 mL, 1.9 mmol) was added to a solution of R/S-4-amino-6-bromo-3,4-dihydro-2,2-dimethyl-2H-1-benzopyran (0.4 g, 1.6 mmol) in methylene chloride (5 mL). After 20 min at room temperature, the resulting precipitate was collected by filtration, washed with petroleum ether 40/60 and dried. The crude product was triturated with ethyl acetate. The insoluble was eliminated by filtration and petroleum ether 40/60 was added to the filtrate. The resulting precipitate was collected by filtration, washed with petroleum ether 40/60 and dried (64%). mp: 196-198° C., IR (KBr): υ: 3324 (N—H), 2977 (C—H aliphatic), 1622 (C═O) cm$^{-1}$, Anal. ($C_{18}H_{18}N_2O_2ClBr$) C, H, N.

EXAMPLE 80

R/S-4-(4-Chlorophenylaminocarbonylamino)-3,4-dihydro-2,2-dimethyl-6-fluoro-2H-1-benzopyran 4-Chlorophenyl isocyanate (0.38 g, 2.4 mmol) was added to a solution of RS-4-amino-3,4-dihydro-2,2-dimethyl-6-fluoro-2H-1-benzopyran (0.4 g, 2 mmol) in methylene chloride (5 mL). After 20 min at room temperature, the resulting precipitate was collected by filtration, washed with petroleum ether 40/60 and dried. The product was then crystallized in a mixture methanol/water. The resulting precipitate was collected by filtration, washed with water and dried. The crude product was triturated with ethyl acetate. The insoluble was eliminated by filtration and petroleum ether 40/60 was added to the filtrate. The resulting precipitate was collected by filtration, washed with petroleum ether 40/60 and dried (35%). mp: 188-189° C., IR (KBr): υ: 3341 (N—H), 2988 (C—H aliphatic), 1634 (C═O) cm$^{-1}$, Anal. ($C_{18}H_{18}N_2O_2FCl$) C, H, N.

EXAMPLE 81

R/S-6-Chloro-4-(4-chlorophenylaminocarbonylamino)-3,4-dihydro-2,2-dimethyl-2H-1-benzopyran 4-Chlorophenyl isocyanate (0.35 g, 2.3 mmol) was added to a solution of R/S-4-amino-6-chloro-3,4-dihydro-2,2-dimethyl-2H-1-benzopyran (0.4 g, 1.9 mmol) in methylene chloride (5 mL). After 20 min at room temperature, the resulting precipitate was collected by filtration, washed with petroleum ether 40/60 and dried. The product was then crystallized in a mixture methanol/water. The resulting precipitate was collected by filtration, washed with water and dried. The crude product was triturated with ethyl acetate. The insoluble was eliminated by filtration and petroleum ether 40/60 was added to the filtrate. The resulting precipitate was collected by filtration, washed with petroleum ether 40/60 and dried (44%). mp: 205-211° C., IR (KBr): υ: 3336 (N—H), 2978, 2930 (C—H aliphatic), 1638 (C═O) cm$^{-1}$, Anal. ($C_{18}H_{18}N_2O_2Cl_2$) C, H, N.

EXAMPLE 82

R/S-6-Bromo-4-(4-chlorophenylaminocarbonylamino)-3,4-dihydro-2,2-dimethyl-2H-1-benzopyran.

4-Chlorophenyl isocyanate (0.29 g, 1.9 mmol) was added to a solution of R/S-4-amino-6-bromo-3,4-dihydro-2,2-dimethyl-2H-1-benzopyran (0.4 g, 1.6 mmol) in methylene chloride (5 mL). After 20 min at room temperature, the resulting precipitate was collected by filteration, washed with petroleum ether 40/40 and dried (878%). Mp: 211-212° C., IR (KBr); υ: 3312 (N—H), 2984, 2950, 2931 (C—H, aliphatic) 1630 (C═O) cm$^{-1}$, Anal. ($C_{18}H_{18}N_2O_2ClBr$) C, H, N.

Biological Essays

The activity of the compounds as potassium channel openers can be measured by measurement of tension in rat aorta rings, measurement of $^{86}Rb$ ($^{42}K$ substitute) outflow from rat aorta rings, measurement of insulin release from incubated rat pancreatic islets together with measurement of 86Rb outflow from perifused rat pancreatic islets.

Measurement of insulin release from incubated rat pancreatic islets was performed according to the following procedure.

Experiments were performed with pancreatic islets isolated from adult fed Wistar rats (Charles River Laboratories, Belgium).

Groups of 10 islets, each derived from the same batch of islets, were preincubated for 30 minutes at 37° C. in 1 mL of a physiological salt medium (in mM: NaCl 115, KCl 5, $CaCl_2$ 2.56, $MgCl_2$ 1, $NaHCO_3$ 24) supplemented with 2.8 mM glucose, 0.5% (w:v) dialyzed albumin (Sigma) and equilibrated against a mixture of $O_2$ (95%) and $CO_2$ (5%). The islets were then incubated at 37° C. for 90 minutes in 1 mL of the same medium containing 16.7 mM glucose and, in addition, the required benzopyran derivative.

The release of insulin was measured radioimmunologically according to Leclercq-Meyer et al., Endocrinology, 1985, 116, 1168-1174 using rat insulin as a standard.

Residual insulin secretion was expressed as a percentage of the value recorded in control experiments (100%); i.e. in the absence of drug and presence of 16.7 mM glucose. Measurement of 86Rb outflow from perifused rat pancreatic islets was performed according to the following procedure. Groups of 100 islets were incubated for 60 min in a medium containing 16.7 mM glucose and 86Rb (0.15-0.25 mM; 50 µCi/ml). After incubation, the islets were washed three times and then placed in a perifusion chamber. The perifusate was delivered at a constant rate (1.0 ml/min). From the 31st to the 90th min, the effluent was continuously collected over successive periods of 1 min each. An aliquot of the effluent (0.6 ml) was used for scintillation counting. At the end of the perifusion, the radioactive content of the islets was determined. The outflow of 86Rb (cpm/min) was expressed as a fractional outflow rate (% of instantaneous islet content/min; FOR).

Measurement of tension in rat aorta rings was performed according to the following procedure.

Experiments were performed with aorta removed from adult fed Wistar rats (Charles River Laboratories, Belgium).

A section of the thoracic aorta was cleared of adhering fat and connective tissue and was cut into transverse rings (3-4 mm long). The endothelium was removed and the segments suspended under 1.5 g tension in an organ bath containing 20 mL of a physiological solution (in mM: NaCl 118, KCl 4.7, $CaCl_2$ 2.5, $NaHCO_3$ 25, $KH_2PO_4$ 1.2, $MgSO_4$ 1.2, glucose 5). The physiological solution was maintained at 37° C. and continuously bubbled with a mixture of $O_2$ (95%) and $CO_2$ (5%). Isometric contractions were measured with a force-displacement transducer. After 60 minutes of equilibration, the rings were exposed to KCl (30 or 80 mM). When the tension had stabilized, the chroman derivative was added to the bath at increasing concentrations until maximal relaxation (or until 300 □M). Some experiments were repeated in the continuous presence of 1 or 10 □M glibenclamide in the bathing medium.

The relaxation response was expressed as the percentage of the contractile response to KCl. The $ED_{50}$ values (concentration evoking 50% inhibition of the plateau phase induced by KCl) were assessed from dose-response curves using Datanalyst software (EMKA Technologies, France).

Measurement of $^{86}Rb$ outflow from rat aorta rings was performed according to the following procedure.

Experiments were performed with thoracic rat aorta rings (2 mm long) isolated from adult fed Wistar rats (Charles River Laboratories, Belgium).

The aorta rings were preincubated for 30 min at 37° C. in a physiological solution (in mM: NaCl 115, KCl 5, $CaCl_2$ 2.56, $MgCl_2$ 1, $NaHCO_3$ 24) equilibrated against a mixture of $O_2$ (95%) and $CO_2$ (5%). After preincubation, the aorta rings were incubated for 60 min at 37° C. in the same medium containing, in addition, $^{86}Rb$ ion (0.15-0.25 mM; 50 microCi $mL^{-1}$). Following incubation, the segments were washed four times with non-radioactive medium and then placed in a perfusion chamber. The perfusate was delivered at a constant rate ($1.0 mL \cdot min^{-1}$). From the $31^{st}$ to the $90^{th}$ min, the effluent was continuously collected over successive periods of 1 min each and examined for its radioactive content by scintillation counting. At the end of the perifusion, the radioactive content of the aortic segments was also determined.

The experiments were conducted in the presence of 30 mM KCl in the perifusing medium to mimic the experimental conditions used to measure muscle tension.

The efflux of $^{86}Rb$ was expressed as a fractional outflow rate (FOR: % of instantaneous aorta content per min).

The validity of $^{86}Rb$ ($^{42}K$ substitute) as a tracer for the study of $K^+$ handling in aorta rings has been previously assessed (Lebrun et al., Pharmacology, 1990, 41, 36-48; Antoine et al., Eur. J. Pharmacol., 1992, 216, 299-306).

In such models, PCOs such as diazoxide, pinacidil and cromakalim have been reported to reduce the glucose-induced insulin output and/or to exhibit myorelaxant activity as described by de Tullio et al., J. Med. Chem., 1996, 39, 937-948.

Table 1 depicts the biological data obtained with the new benzopyran derivatives. Cromakalim, diazoxide and pinacidil were used as reference compounds.

TABLE 1

Effects of new benzopyran derivatives on insulin secretion from rat pancreatic islets and on the contractile activity of rat aorta rings. Results are expressed as mean ± s.e.m., n refers to the number of samples.

| Compounds | X | Y | Residual insulin secretion (%) [10 µM] | Myorelaxant activity $ED_{50}$ (µM) |
|---|---|---|---|---|
| (structure shown below) | F | 3-chlorophenyl | 28.0 ± 1.5 (23) | >300 (4) |
| | Br | 4-chlorophenyl | 25.7 ± 1.5 (23) | >300 (4) |

Structure: chroman-4-yl urea derivative with X substituent on benzene ring, Y substituent on terminal nitrogen, and 2,2-dimethyl groups on the chroman.

TABLE 1-continued

Effects of new benzopyran derivatives on insulin secretion from rat pancreatic islets and on the contractile activity of rat aorta rings. Results are expressed as mean ± s.e.m., n refers to the number of samples.

| Compounds | X | Y | Residual insulin secretion (%) [10 µM] | Myorelaxant activity $ED_{50}$ (µM) |
|---|---|---|---|---|
| 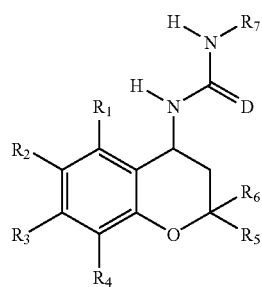 | F | 3-methylphenyl | 53.1 ± 3.6 (24) | 7.3 ± 0.8 (4) |
| | Cl | 4-methylphenyl | 32.8 ± 1.9 (16) | >30 (4) |
| | F | 3-methoxyphenyl | 52.0 ± 2.3 (24) | 6.2 ± 0.6 (4) |
| | Br | 3-pyridyl | 44.3 ± 2.8 (23) | 0.368 ± 0.029 (4) |
| Cromakalim | — | — | 94.7 ± 4.3 (24) | 0.13 ± 0.01 (7) |
| Diazoxide | — | — | 71.7 ± 2.8 (38)[b] | 23.8 ± 2.4 (10)[b] |
| Pinacidil | — | — | 96.0 ± 4.2 (20)[c] | 0.35 ± 0.02 (11) |

[a]nd: not determined.
Published results:
[b]ref. Becker et al., Br. J. Pharmacol, 2001, 134, 375-385;
[c]ref. Lebrun et al. J. Pharmacol, Exp. Ther., 1996, 277, 156-162.

Results obtained on rat pancreatic islets indicated that the benzopyran derivatives inhibited insulin secretion or expressed myorelaxant activity.

According to the chemical structure of the drugs, the nature of the substituent in the 4-position appeared to be important for the inhibitory effect on insulin release.

The benzopyran derivatives according to the invention are effective over a wide dosage range. In general satisfactory results are obtained with dosage from 0.05 to 1000 milligrams of a benzopyran derivative of formula I, compounded with physiologically acceptable vehicle, carrier, excipient, binder, preservative, stabilizer, flavor and the like in a unit dosage form as called for by accepted pharmaceutical practice. The exact dosage depends upon a lot of factors such as mode of administration and form in which it is administered.

The invention claimed is:

1. Benzopyran derivatives of the general formula (I)

wherein:
D represents S or O;
$R_1$, $R_2$, $R_3$ and $R_4$ are independently hydrogen, halogen, $C_{1-6}$-alkyl, $C_{3-8}$-cycloalkyl, hydroxy, $C_{1-6}$-alkoxy, $C_{1-6}$-alkoxy-$C_{1-6}$-alkyl, nitro, amino, cyano, cyanomethyl, perhalomethyl, $C_{1-6}$-monoalkyl- or dialkylamino, sulfamoyl, $C_{1-6}$-alkylthio, $C_{1-6}$-alkylsulfonyl, $C_{1-6}$-alkylsulfinyl, formyl, $C_{1-6}$-alkylcarbonylamino, $R_8$arylthio, $R_8$arylsulfinyl, $R_8$arylsulfonyl, $C_{1-6}$-alkoxycarbonyl, $C_{1-6}$-alkoxycarbonyl-$C_{1-6}$-alkyl, carbamoyl, carbamoylmethyl, $C_{1-6}$-monoalkyl- or dialkylaminocarbonyl, $C_{1-6}$-monoalkyl- or dialkylaminothiocarbonyl, ureido, $C_{1-6}$-monoalkyl- or dialkylaminocarbonylamino, thioureido, $C_{1-6}$-monoalkyl- or dialkylaminothiocarbonylamino, $C_{1-6}$-monoalkyl- or dialkylaminosulfonyl, carboxy, carboxy-$C_{1-6}$-alkyl, acyl, $R_8$aryl, $R_8$aryl-$C_{1-6}$-alkyl, $R_8$aryloxy;

$R_5$ and $R_6$ are each independently hydrogen, $C_{1-6}$-alkyl or, $R_5$ and $R_6$ taken together with the carbon atom to which they are attached form a 3- to 6-membered carbocyclic ring;

$R_7$ is 2-, 3- or 4-pyridyl optionally mono- or polysubstituted by $R_1$ or $R_7$ is 2- or 3-thienyl optionally mono- or polysubstituted substituted by $R_1$ or $R_7$ is phenyl mono- or polysubstituted by $R_1$ with the exception of $R_7$ representing $C_6H_5$;

$R_8$ is hydrogen, halogen, $C_{1-6}$-alkyl, $C_{3-8}$-cycloalkyl, hydroxy, $C_{1-6}$-alkoxy, nitro, amino, cyano, cyanomethyl, perhalomethyl;

or a salt thereof with a pharmaceutically acceptable acid or base, or any optical isomer or mixture of optical isomers, including a racemic mixture or any polymorphic and tautomeric form.

2. The benzopyran derivative according to claim 1 wherein D represents S.

3. The benzopyran derivative according to claim 1 selected from:
R/S-4-(3-Chlorophenylaminothiocarbonylamino)-3,4-dihydro-2,2-dimethyl-6-fluoro-2H-1-benzopyran,
R/S-6-Chloro-4-(3-chlorophenylaminothiocarbonylamino)-3,4-dihydro-2,2-dimethyl-2H-1-benzopyran,
R/S-4-(4-Chlorophenylaminothiocarbonylamino)-3,4-dihydro-2,2-dimethyl-6-fluoro-2H-1-benzopyran,
R/S-6-Chloro-4-(4-chlorophenylaminothiocarbonylamino)-3,4-dihydro-2,2-dimethyl-2H-1-benzopyran,
R/S-6-Bromo-4-(4-chlorophenylaminothiocarbonylamino)-3,4-dihydro-2,2-dimethyl-2H-1-benzopyran, R/S-4-(3-Cyanophenylaminothiocarbonylamino)-3,4-dihydro-2,2-dimethyl-6-fluoro-2H-1-benzopyran,
R/S-6-Chloro-4-(3-cyanophenylaminothiocarbonylamino)-3,4-dihydro-2,2-dimethyl-2H-1-benzopyran,
R/S-6-Bromo-4-(3-cyanophenylaminothiocarbonylamino)-3,4-dihydro-2,2-dimethyl-2H-1-benzopyran,
R/S-4-(4-Cyanophenylaminothiocarbonylamino)-3,4-dihydro-2,2-dimethyl-6-fluoro-2H-1-benzopyran,
R/S-6-Chloro-4-(4-cyanophenylaminothiocarbonylamino)-3,4-dihydro-2,2-dimethyl-2H-1-benzopyran,
R/S-6-Bromo-4-(4-cyanophenylaminothiocarbonylamino)-3,4-dihydro-2,2-dimethyl-2H-1-benzopyran,
R/S-6-Chloro-3,4-dihydro-2,2-dimethyl-4-(3-nitrophenylaminothiocarbonylamino)-2H-1-benzopyran,
R/S-6-Bromo-3,4-dihydro-2,2-dimethyl-4-(3-nitrophenylaminothiocarbonylamino)-2H-1-benzopyran,
R/S-3,4-Dihydro-2,2-dimethyl-6-fluoro-4-(4-nitrophenylaminothiocarbonylamino)-2H-1-benzopyran,
R/S-6-Chloro-3,4-dihydro-2,2-dimethyl-4-(4-nitrophenylaminothiocarbonylamino)-2H-1-benzopyran,
R/S-4-(3-Chlorophenylaminothiocarbonylamino)-3,4-dihydro-2,2-dimethyl-6-fluoro-2H-1-benzopyran,
R/S-6-Chloro-4-(3-chlorophenylaminothiocarbonylamino)-3,4-dihydro-2,2-dimethyl-2H-1-benzopyran,
R/S-4-(4-Chlorophenylaminothiocarbonylamino)-3,4-dihydro-2,2-dimethyl-6-fluoro-2H-1-benzopyran,
R/S-6-Chloro-4-(4-chlorophenylaminothiocarbonylamino)-3,4-dihydro-2,2-dimethyl-2H-1-benzopyran,
R/S-6-Bromo-4-(4-chlorophenylaminothiocarbonylamino)-3,4-dihydro-2,2-dimethyl-2H-1-benzopyran,
R/S-4-(3-Cyanophenylaminothiocarbonylamino)-3,4-dihydro-2,2-dimethyl-6-fluoro-2H-1-benzopyran,
R/S-6-Chloro-4-(3-cyanophenylaminothiocarbonylamino)-3,4-dihydro-2,2-dimethyl-2H-1-benzopyran,
R/S-6-Bromo-4-(3-cyanophenylaminothiocarbonylamino)-3,4-dihydro-2,2-dimethyl-2H-1-benzopyran,
R/S-4-(4-Cyanophenylaminothiocarbonylamino)-3,4-dihydro-2,2-dimethyl-6-fluoro-2H-1-benzopyran,
R/S-6-Chloro-4-(4-cyanophenylaminothiocarbonylamino)-3,4-dihydro-2,2-dimethyl-2H-1-benzopyran,
R/S-6-Bromo-4-(4-cyanophenylaminothiocarbonylamino)-3,4-dihydro-2,2-dimethyl-2H-1-benzopyran,
R/S-6-Chloro-3,4-dihydro-2,2-dimethyl-4-(3-nitrophenylaminothiocarbonylamino)-2H-1-benzopyran,
R/S-6-Bromo-3,4-dihydro-2,2-dimethyl-4-(3-nitrophenylaminothiocarbonylamino)-2H-1-benzopyran,
R/S-3,4-Dihydro-2,2-dimethyl-6-fluoro-4-(4-nitrophenylaminothiocarbonylamino)-2H-1-benzopyran,
R/S-6-Chloro-3,4-dihydro-2,2-dimethyl-4-(4-nitrophenylaminothiocarbonylamino)-2H-1-benzopyran,
R/S-6-Bromo-3,4-dihydro-2,2-dimethyl-4-(4-nitrophenylaminothiocarbonylamino)-2H-1-benzopyran,
R/S-6-Bromo-3,4-dihydro-2,2-dimethyl-4-(4-nitrophenylaminothiocarbonylamino)-2H-1-benzopyran,
R/S-6-Bromo-3,4-dihydro-2,2-dimethyl-4-(3-trifluoromethylphenylaminothiocarbonylamino)-2H-1-benzopyran,
R/S-6-Chloro-3,4-dihydro-2,2-dimethyl-4-(2-methoxyphenylaminocarbonylamino)-2H-1-benzopyran,
R/S-6-Bromo-3,4-dihydro-2,2-dimethyl-4-(2-methoxyphenylaminocarbonylamino)-2H-1-benzopyran,
R/S-3,4-Dihydro-2,2-dimethyl-6-fluoro-4-(3-methoxyphenylaminocarbonylamino)-2H-1-benzopyran,
R/S-6-Chloro-3,4-dihydro-2,2-dimethyl-4-(3-methoxyphenylaminocarbonylamino)-2H-1-benzopyran,
R/S-6-Bromo-3,4-dihydro-2,2-dimethyl-4-(3-methoxyphenylaminocarbonylamino)-2H-1-benzopyran,
R/S-3,4-Dihydro-2,2-dimethyl-6-fluoro-4-(4-methoxyphenylaminocarbonylamino)-2H-1-benzopyran,
R/S-6-Chloro-3,4-dihydro-2,2-dimethyl-4-(4-methoxyphenylaminocarbonylamino)-2H-1-benzopyran,
R/S-6-Bromo-3,4-dihydro-2,2-dimethyl-4-(4-methoxyphenylaminocarbonylamino)-2H-1-benzopyran,
R/S-3,4-Dihydro-2,2-dimethyl-6-fluoro-4-(2-methylphenylaminocarbonylamino)-2H-1-benzopyran,
R/S-6-Chloro-3,4-dihydro-2,2-dimethyl-4-(2-methylphenylaminocarbonylamino)-2H-1-benzopyran,
R/S-6-Bromo-3,4-dihydro-2,2-dimethyl-4-(2-methylphenylaminocarbonylamino)-2H-1-benzopyran,
R/S-3,4-Dihydro-2,2-dimethyl-6-fluoro-4-(3-methylphenylaminocarbonylamino)-2H-1-benzopyran,
R/S-6-Chloro-3,4-dihydro-2,2-dimethyl-4-(3-methylphenylaminocarbonylamino)-2H-1-benzopyran,
R/S-6-Bromo-3,4-dihydro-2,2-dimethyl-4-(3-methylphenylaminocarbonylamino)-2H-1-benzopyran,
R/S-3,4-Dihydro-2,2-dimethyl-6-fluoro-4-(4-methylphenylaminocarbonylamino)-2H-1-benzopyran,
R/S-6-Chloro-3,4-dihydro-2,2-dimethyl-4-(4-methylphenylaminocarbonylamino)-2H-1-benzopyran,
R/S-6-Bromo-3,4-dihydro-2,2-dimethyl-4-(4-methylphenylaminocarbonylamino)-2H-1-benzopyran,
R/S-4-(2-Chlorophenylaminocarbonylamino)-3,4-dihydro-2,2-dimethyl-6-fluoro-2H-1-benzopyran,
R/S-6-Chloro-4-(2-chlorophenylaminocarbonylamino)-3,4-dihydro-2,2-dimethyl-2H-1-benzopyran,
R/S-6-Bromo-4-(2-chlorophenylaminocarbonylamino)-3,4-dihydro-2,2-dimethyl-2H-1-benzopyran,
R/S-4-(3-Chlorophenylaminocarbonylamino)-3,4-dihydro-2,2-dimethyl-6-fluoro-2H-1-benzopyran,
R/S-6-Chloro-4-(3-chlorophenylaminocarbonylamino)-3,4-dihydro-2,2-dimethyl-2H-1-benzopyran,
R/S-6-Bromo-4-(3-chlorophenylaminocarbonylamino)-3,4-dihydro-2,2-dimethyl-2H-1-benzopyran,
R/S-4-(4-Chlorophenylaminocarbonylamino)-3,4-dihydro-2,2-dimethyl-6-fluoro-2H-1-benzopyran,
R/S-6-Chloro-4-(4-chlorophenylaminocarbonylamino)-3,4-dihydro-2,2-dimethyl-2H-1-benzopyran,
R/S-6-Bromo-4-(4-chlorophenylaminocarbonylamino)-3,4-dihydro-2,2-dimethyl-2H-1-benzopyran.

4. The pharmaceutical composition comprising a benzopyran derivative according to claim 1 or pharmaceutically acceptable salt thereof with a pharmaceutically acceptable acid or base or any optical isomer or mixture of optical isomers, including a racemic mixture or any tautomeric form together with one or more pharmaceutically acceptable carriers of diluents.

5. The pharmaceutical composition according to claim 4 in the form of an oral dosage unit or parental dosage unit.

6. The pharmaceutical composition according to claim 4 in the form of an oral dosage unit or parental dosage unit containing said benzopyran derivative in a range from about 0.05 to 1000 mg per day.

7. The method of treating diseases of the endocrinological system, selected from hyperinsulinaemia and diabetes in a subject in need thereof comprising administering an effective amount of a benzopyran derivative according to claim 1.

8. The process for the manufacture of a medicament, particular to be used in the treatment of diseases of the endocrinological system, selected from hyperinsulinaemia and diabetes which process comprising bringing a compound of formula (I) according to claim 1 or a pharmaceutically acceptable salt thereof into a galenic dosage form.

9. A method of preparing a benzopyran derivative of formula (I) which comprises:

reacting a compound of formula (II)

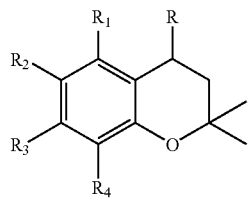

(II)

wherein R represents NH$_2$ and R$_1$, R$_2$, R$_3$ and R$_4$ are defined as for formula (I) with an isothiocyanante of formula (III)

R$_7$—N═C═D   (III)

wherein D represents S or O and R$_7$ is defined as for formula (I), to form a benzopyran derivative of formula (I); or reacting a compound of formula (II) wherein R represents —N═C═S and R$_1$, R$_2$, R$_3$ and R$_4$ are defined as for formula (I) with an amine of formula (IV)

R$_7$—NH$_2$   (IV)

wherein R$_7$ is defined as for formula (I), to form a benzopyran derivative of formula (I).

10. The pharmaceutical composition according to claim 4 in the form of an oral dosage unit or parental dosage unit containing said benzopyran derivative in a range from about 0.1 to 500.

11. The pharmaceutical composition according to claim 4 in the form of an oral dosage unit or parental dosage unit containing said benzopyran derivative in a range from about 50 to 200 mg per day.

12. The method of claim 7 wherein the benzopyran derivative is administered as a dose in a range from about 0.05 to 1000 mg per day.

13. The method of claim 7 wherein the benzopyran derivative is administered as a dose in a range from about 0.1 to 500 mg per day.

14. The method of claim 7 wherein the benzopyran derivative is administered as a dose in a range from about 50 to 200 mg per day.

* * * * *